United States Patent [19]

Pfefferle et al.

[11] Patent Number: 6,133,000

[45] Date of Patent: *Oct. 17, 2000

[54] FERMENTATIVE PREPARATION OF AMINO ACIDS

[75] Inventors: Walter Pfefferle, Halle; Hermann Lotter, Hainburg; Heinz Friedrich, Hanau; Wolfgang Degener, Bielefeld, all of Germany

[73] Assignee: Degussa-Hüls Aktiengesellschaft, Frankfurt, Germany

[*] Notice: This patent is subject to a terminal disclaimer.

[21] Appl. No.: 09/087,969

[22] Filed: Jun. 1, 1998

Related U.S. Application Data

[63] Continuation-in-part of application No. 08/677,911, Jul. 10, 1996, Pat. No. 5,770,409, which is a continuation of application No. 08/198,374, Feb. 18, 1994, abandoned, which is a continuation of application No. 07/942,804, Sep. 10, 1992, abandoned.

[30] Foreign Application Priority Data

Sep. 17, 1991 [DE] Germany ............................. 41 30 867

[51] Int. Cl.$^7$ ...................................................... C12P 13/08
[52] U.S. Cl. ........................ 435/115; 435/106; 435/252.1
[58] Field of Search ..................................... 435/115, 106, 435/252.1

[56] References Cited

U.S. PATENT DOCUMENTS

| | | | |
|---|---|---|---|
| 4,411,997 | 10/1983 | Shimazake | ............................. 435/115 |
| 5,133,976 | 7/1992 | Rouy | ............................................ 426/2 |
| 5,639,658 | 6/1997 | Drobish et al. | .......................... 435/243 |

FOREIGN PATENT DOCUMENTS

| | | | |
|---|---|---|---|
| 2488273 | 2/1982 | France . | |
| 2604447 | 4/1988 | France . | |
| 268834 | 6/1989 | Germany . | |
| 269167 | 6/1989 | Germany | ................................ 435/115 |

OTHER PUBLICATIONS

Inbar, L., et al. "Natural–abundance $^{13}C$ Nuclear Magnetic . . . Brevibacterium flavum", Eur. J. Biochem., vol. 149, pp. 601–607, 1985.

Primary Examiner—Irene Marx
Attorney, Agent, or Firm—Smith Gambrell & Russell, LLP

[57] ABSTRACT

A process is disclosed for the fermentative preparation of amino acids, in which an L-lysine producing bacterial strain of the species Corynebacterium glutamicum is cultivated in a nutrient medium and the amino acids can be isolated from the culture medium at the end of fermentation. After the vigorous growth phase, the bacterial culture has at its disposal a smaller quantity of assimilable carbon source than it could metabolize on the basis of the structure of the strain and the quanitity of other necessary supplements provided in the nutrient medium.

12 Claims, 17 Drawing Sheets

FERMENTATIVE PREPARATION OF AMINO ACIDS

This application is a continuation-in-part of U.S. patent application Ser. No. 08/677,911 filed Jul. 10, 1996, (now U.S. Pat. No. 5,770,409), which is a continuation of Ser. No. 08/198,374 filed Feb. 18, 1994, now abandoned, which is a continuation of Ser. No. 07/942,804 filed Sep. 10, 1992, now abandoned.

BACKGROUND AND INTRODUCTION

The present invention relates to a process for the fermentative preparation of amino acids such as L-lysine or L-threonine in which a strain of the bacterial genus Brevibacterium or Corynebacterium producing one or more amino acids is cultivated in a nutrient medium, and the amino acids produced are isolated from the culture fluid at the end of fermentation.

L-lysine is an essential amino acid and is used in large quantities as animal feed supplement. Numerous amino acids are generally produced biosynthetically which has long been known in the art. The bacterial strains for producing amino acids are distinguished by their capacity for secreting these amino acids into the culture medium at high concentrations within a short time. Feed batch processes are generally carried out to avoid high initial concentrations of substrate. Due to the very high metabolic capacity of production strains used, it is of decisive importance to carry out the fermentation process in such a manner that the maximum values of oxygen requirement and of evolution of heat will be of an economically acceptable order of magnitude. Various strategies have therefore been employed to regulate the metabolic activity of the organisms so as to ensure the supply of oxygen and removal of heat and at the same time balance the distribution of formation of biomass and of product.

A process entailing intermittent feeding is disclosed in CSFR-PS 212 558 in which the metabolic activity during the growth phase is adjusted by changes in pH and the total amount of biomass is adjusted by the α-aminonitrogen. Soviet Patent 157 059 describes a process entailing intermittent feeding, in which the threonine concentration serves as the criterion for the feeding and the proportion of the reducing compound is maintained at 3 to 5%. A very finely adjusted process is disclosed in French Patent 8303487. In this process, two feed solutions are continuously added: a leucine phosphate solution which is added at such a rate that both the intensity of metabolism and the formation of the biomass are limited by the rate of addition of supplement. The second feed solution, a sugar solution, is supplied at such a rate that the actual sugar concentration is maintained at 5 to 15 g/l. This process shows that due to a limitation by the leucine/phosphate supplements during the feed phase, the culture uses less sugar at any point in time than is available in the culture medium. This procedure is in line with the repeatedly documented view that both carbon-limitation (C-limitation) and undue carbon-excess (C-excess) should be avoided (e.g., East German Patent 269 167). Hadj Sassi et al. in "Biotechn. Letters," Volume 10, No. 8, pages 583–586 (1988) even propose from 90 to 140 g/l of glucose for this purpose. The metabolic activity is therefore always regulated by a factor other than that of the source of carbon.

Taxonomic Status of Corynebacterium glutamicum

Corynebacterium glutamicum ATCC 13032 (DSM 20300, IFO 12168, JCM 1318, NCIB 10025) was isolated by Kinoshita, 1957, from sewage and has been described by Kinoshita et al., 1958 as Micrococcus glutamicum. Later the strain was transferred to the genus Corynebacterium by Abe et al., 1967. Today Corynebacterium glutamicum (Kinoshita, Nakayama and Akita, 1958) (Abe, Takayama and Kinoshita, 1967) is found in the Approved Lists of Bacterial Names in the genus Corynebacterium, strain ATCC 13032 is designated as type strain of this species.

Corynebacterium glutamicum and some other coryneform bacteria are listed by Kinoshita, 1985, among the L-glutamic acid producing bacteria. Many strains of this species are found in U.S. Patent Bibliographic Database, 1997, or listed in the ATCC and DSMZ catalogues of strains as patent strains. Recently two other glutamic acid producing validly described coryneform bacteria have been classified to C. glutamicum i.e. ATCC $15990^T$ Corynebacterium lilium, Lee and Good, 1963, and ATCC $14020^T$ Brevibacteriurn divaricatum, Su and Yamada 1960, Corynebacterium lilium ATCC 15990 has been isolated by Lee and Good, 1963, and was officially described by Yamada and Komagata, 1972, whereas Brevibacterium divaricatum ATCC $_{14020}{}^T$ was isolated and described by Sue and Yamada, 1960. Both names were listed among the validly described bacteria in the Approved List of Bacterial Names.

Suzuki and coworker (1981) found in their DNA-DNA pairing studies on glutamic acid producing corynebacteria that C. lilium, ATCC $15990^T$ and C. glutarniculn, ATCC $13032^T$ showed 80% DNA-DNA homology to each other. Based on the results of Suzuki and their own studies Liebl and coworker (1991) transferred Corynebacterium lilium (DSM 20137=ATCC $15990^T$) and B. divaricatum (DSM 20297=ATCC $14020^T$) as subjective synonyms to the species Corynebacterium glutamicum. In the same study three unclassified brevibacteria strains i.e. "Brevibacterium flavum" (DSM 20411=ATCC 14067), "B. lactofermentum" (DSM 1312=ATCC 13869) and (DSM 20142=ATCC 13655) were studied too. All three strains could be classified to C. glutamicum on their high DNA/DNA homology to this species. In 1987, D. Collins transferred Brevibacterium ammoniagenes (Cooke and Keith) to the genus Corynebacterium as C. ainmoniagenes (ATCC 6871). In addition, two wrongly classified Corynebacterium ammoniagenes strains i.e. ATCC 13745 and ATCC 13746 could be classified to C. glutamicum in this study too.

The classification of Micrococcus glutamicum to Corynebacterium glutamicum and the transfer of many other wrongly classified glutamic acid producing coryneform bacteria by DNA/DNA reassociation studies to this species was later confirmed and emended by Kampfer et al., in a study of 604 coryneform strains using 280 physiological characters for their numerical classification. The same results were obtained in a numerical analysis of fatty acid patterns of the genus Corynebacterium and related taxa by Kampfer and Kroppenstedt 1996. The phylogenetic analysis of the genus Corynebacterium based on the 16S rDNA gene sequence comparison carried out by Pascual et al. (1995) underlined the affiliation of Corynebacterium glutamicum to this genus.

Based on molecular biological studies (DNA/DNA reassociation and 16S rDNA sequencing) on chemotaxonomical studies (analysis of fatty acid patterns) and studies of phenetic markers (physiological tests) there is no doubt that in addition to the type strain of Corynebacterlium glutamicum ATCC 13032 other glutamic producing strains i.e. ATCC 15990 (C. lilium), ATCC 14020 (Brevibacterium divaricatum), ATCC 14067 ("B. flavum"), ATCC 13869 ("B. lactofermentum") and two wrongly classified strains of Corynebacterium ammoniagenes ATCC 13745 and ATCC 13746 belong to the species Corynebacterium glutamicum.

SUMMARY OF THE INVENTION

It is an object of the present invention to provide a process for the fermentative preparation of amino acids which proceeds at a higher degree of conversion of the source of carbon used (sugar) and in which a higher concentration of amino acids is obtained in the dry mass free from biomass.

This and other objects are achieved by a process for the fermentative preparation of amino acids in which a strain of the bacterial genus Brevibacterium or Corynebacterium producing one or more amino acids is cultivated in a nutrient medium, and the amino acids produced are isolated from the culture fluid at the end of fermentation. It is a feature of the present invention that after vigorous growth phase (during the production phase) a smaller quantity of utilizable source of carbon is available to the bacterial culture than it could usually metabolize based on the structure of the strain and the quantity of other necessary supplements provided in the nutrient medium. The fermentation (nutrient) medium is in other respects of conventional composition.

DETAILED DESCRIPTION OF THE INVENTION

Figure 1:
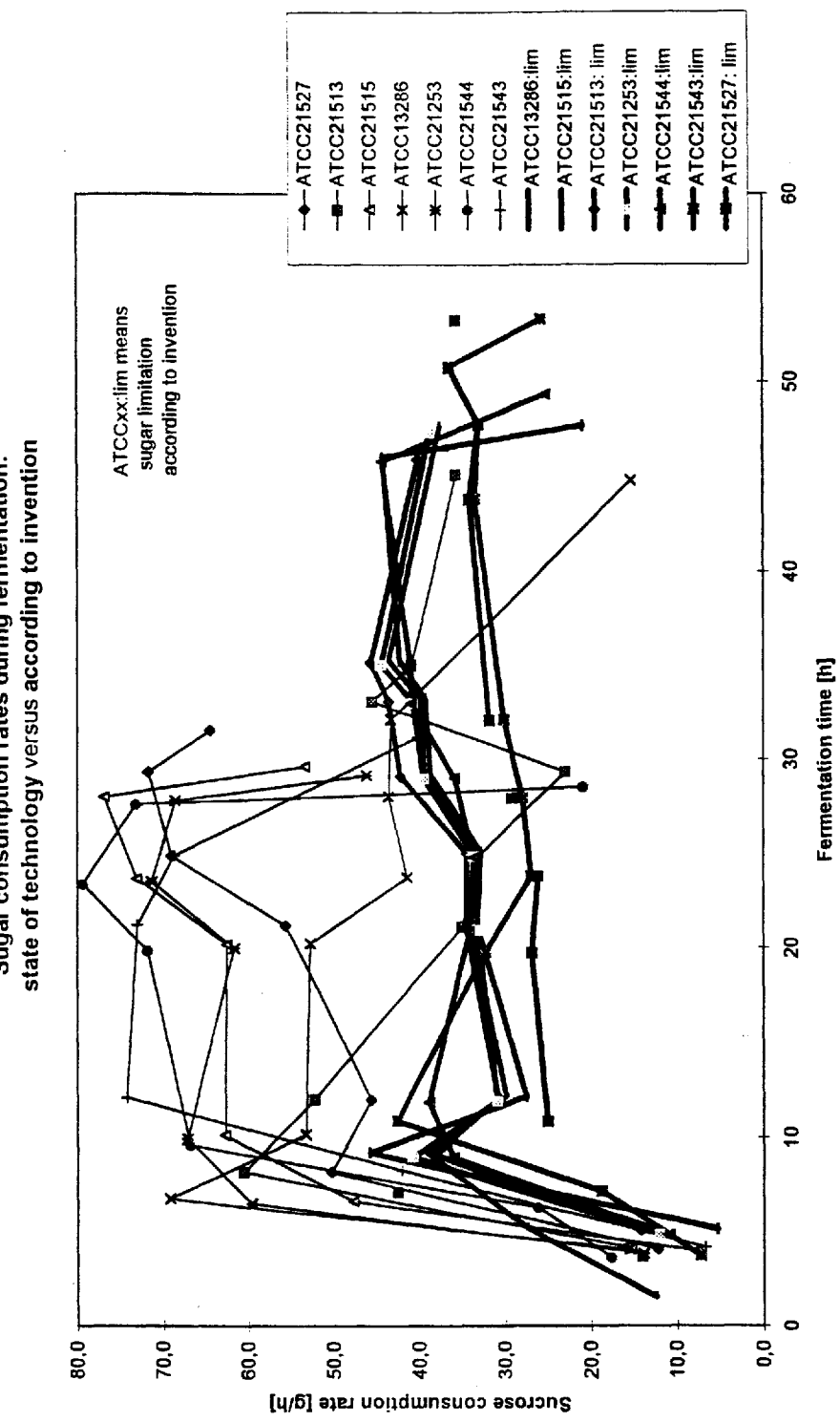
FIG. 1 is a comparison of sugar consumption rates during fermentation for the process of the state of the technology versus the process of the invention for various strains. The legend (lim) following the ATCC strain number denotes that the results were obtained under the sugar limiting conditions of the process of the invention.
Figure 2:
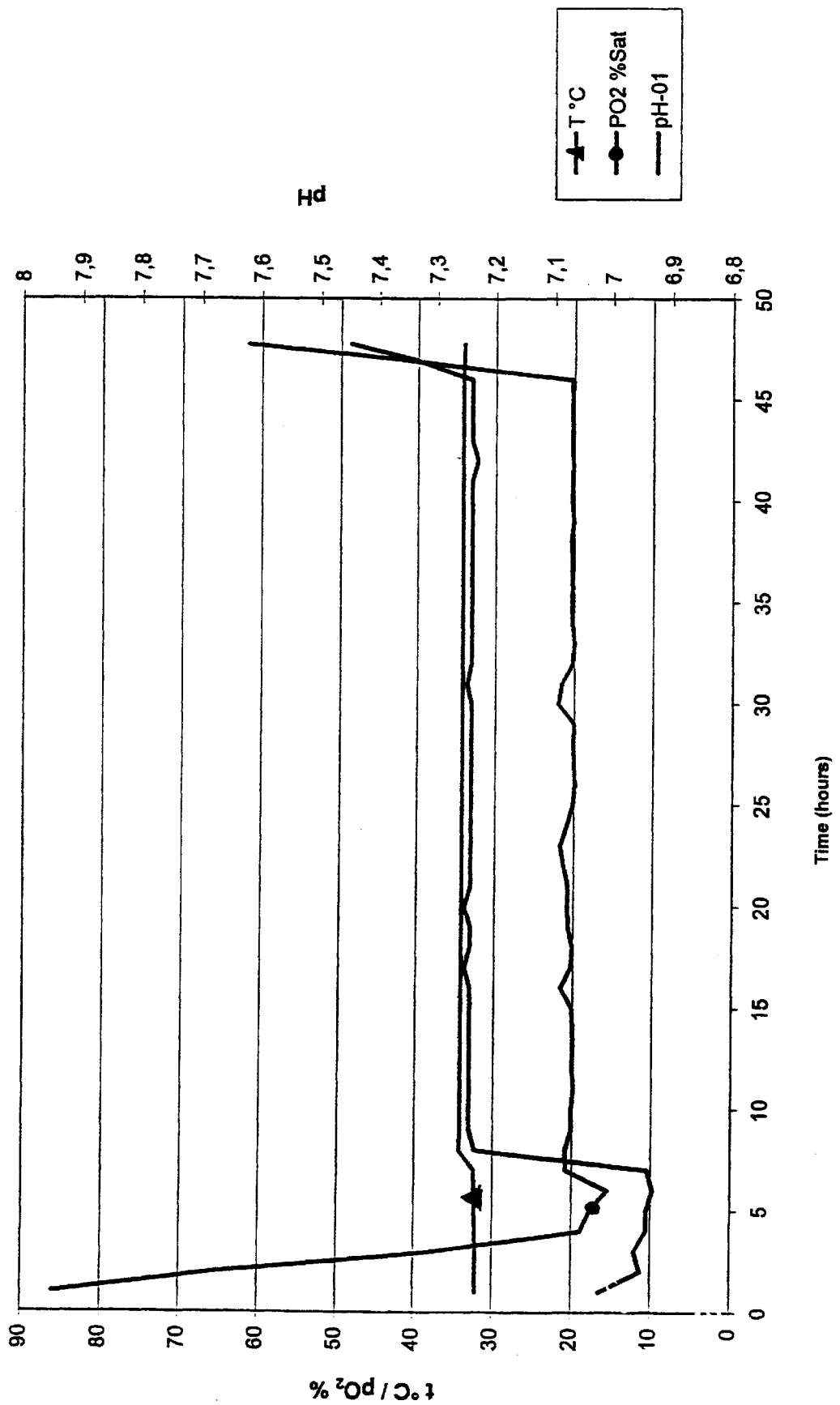
FIG. 2 shows the conditions of temperature, dissolved oxygen and pH during the fermentation of strain ATCC 13286 by the process of the invention in Example 7.
Figure 3:
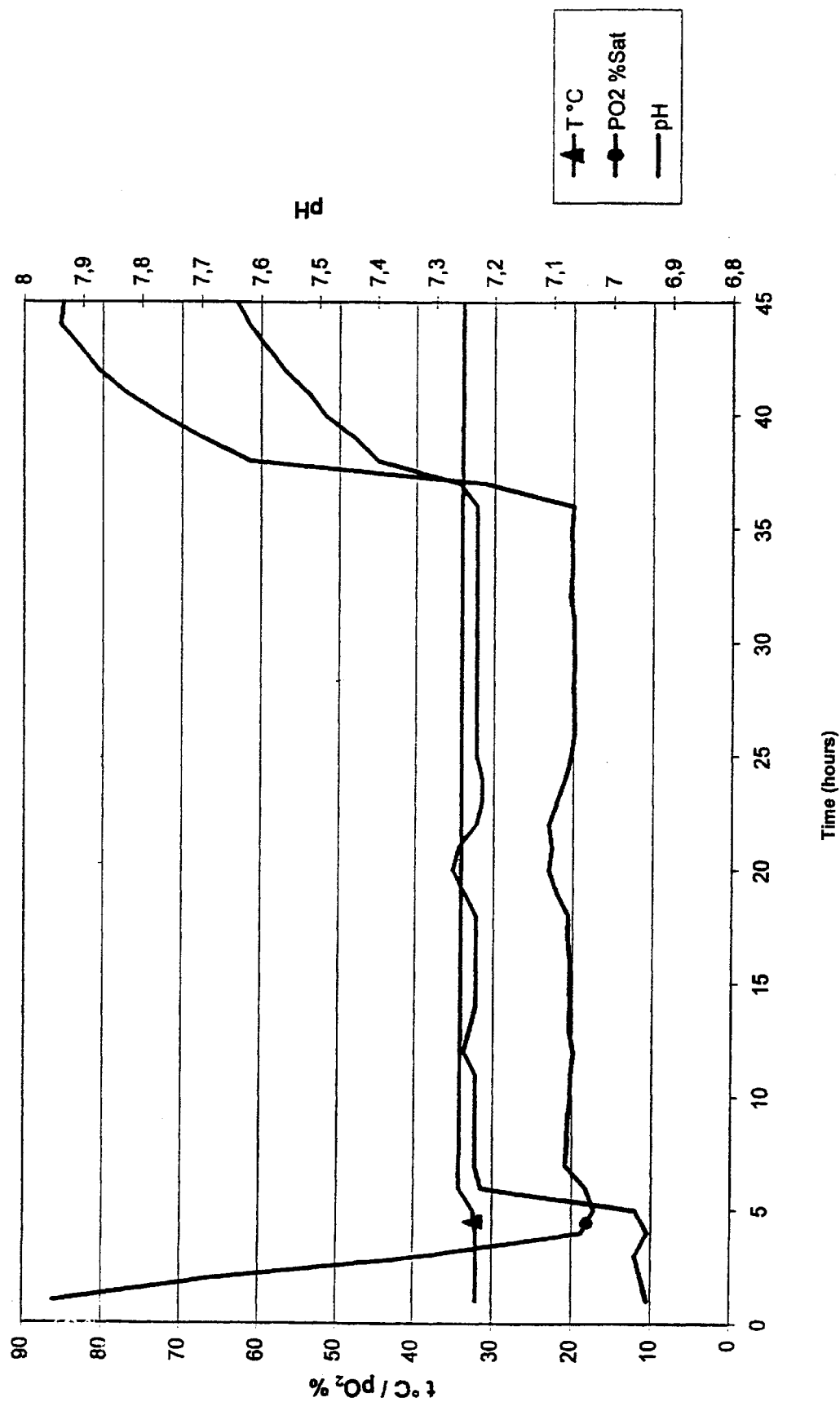
FIG. 3 shows the conditions of temperature, dissolved oxygen and pH during the fermentation of strain ATCC 13286 by the process according to the state of the art (sucrose >5 g/l) in Example 7.
Figure 4:
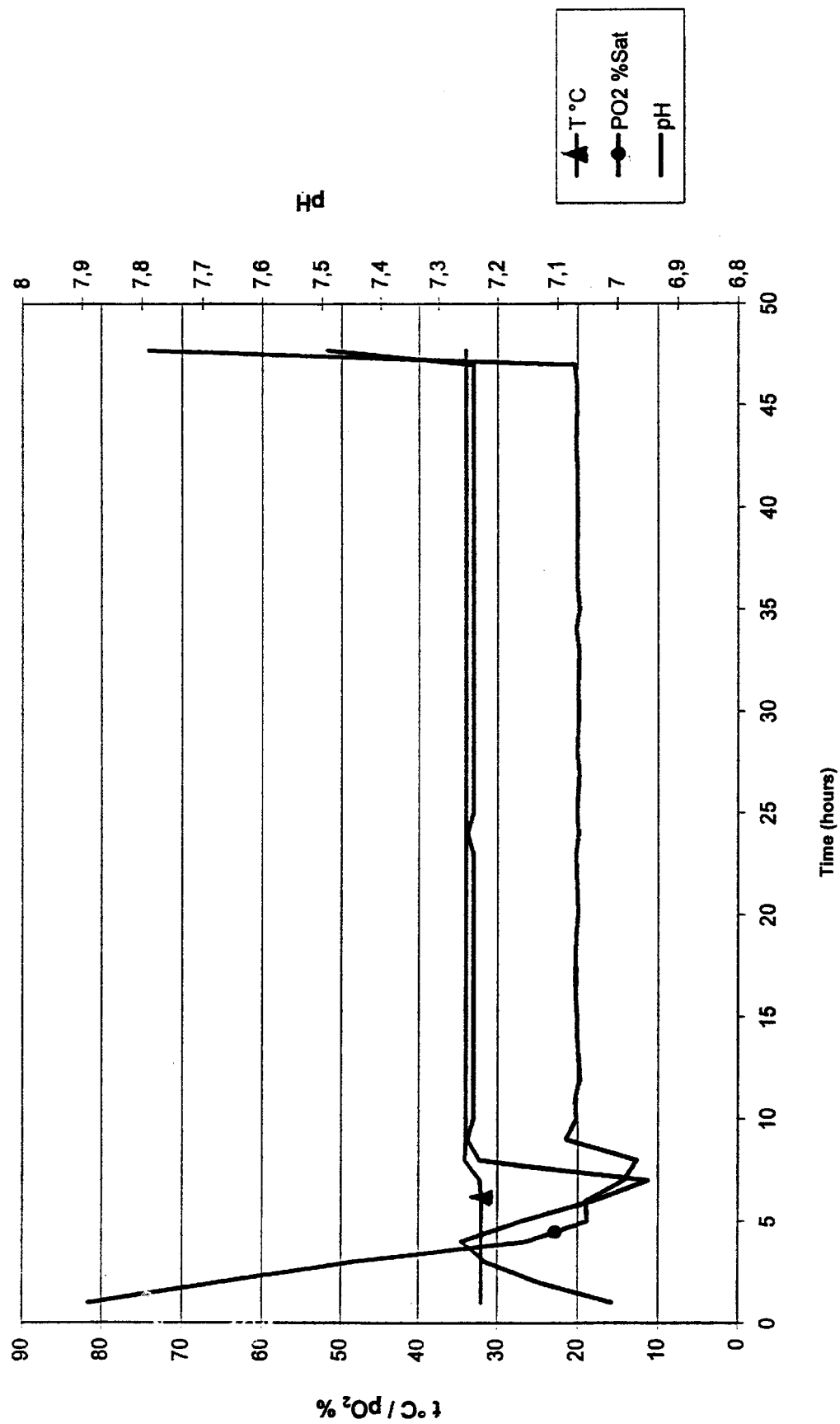
FIG. 4 shows the conditions of temperature, dissolved oxygen and pH during the fermentation of strain ATCC 21515 by the process of the invention in Example 7.
Figure 5:
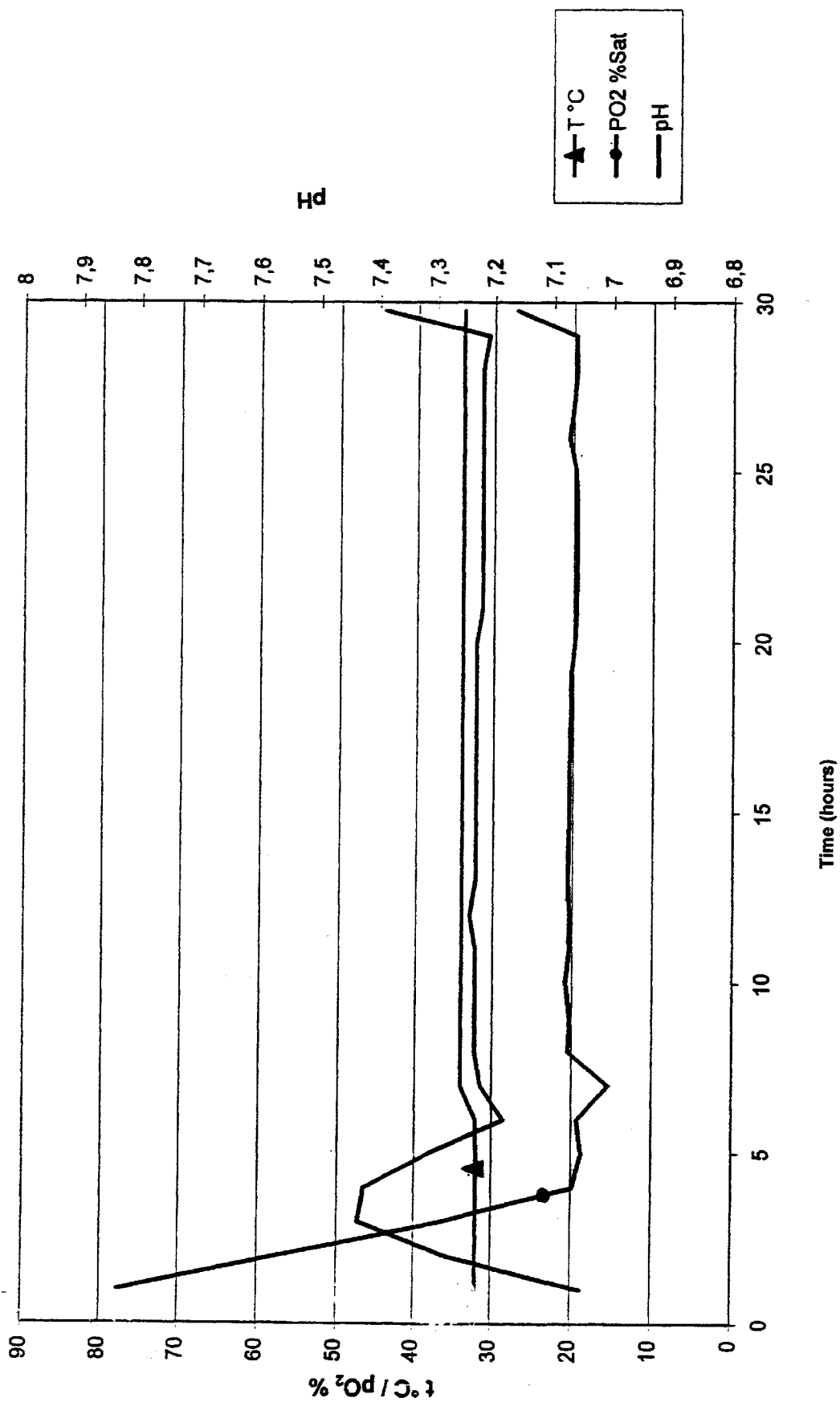
FIG. 5 shows the conditions of temperature, dissolved oxygen and pH during the fermentation of strain ATCC 21515 by the process according to the state of the art (sucrose >5 g/l) in Example 7.
Figure 6:
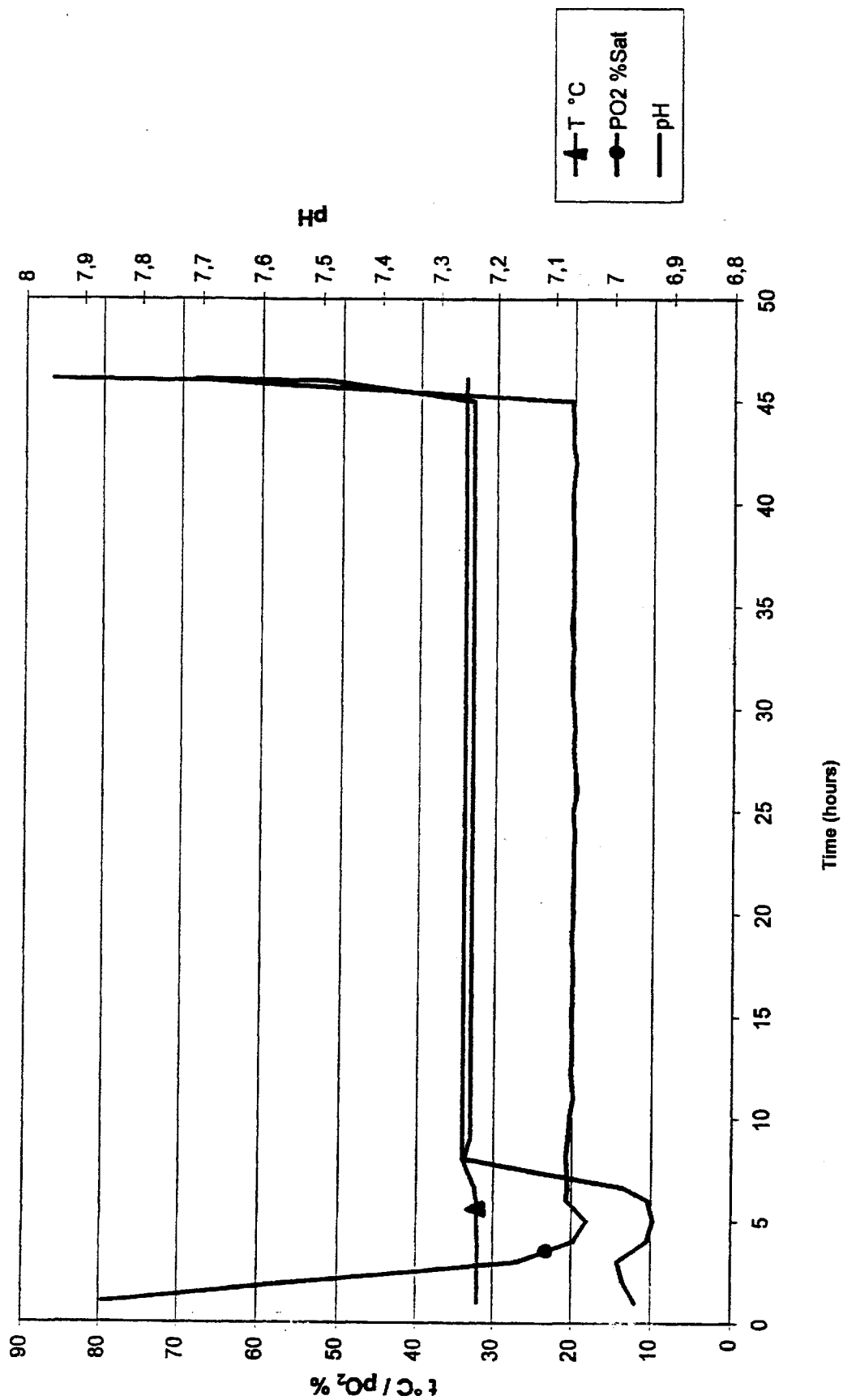
FIG. 6 shows the conditions of temperature, dissolved oxygen and pH during the fermentation of strain ATCC 21513 by the process of the invention in Example 7.
Figure 7:
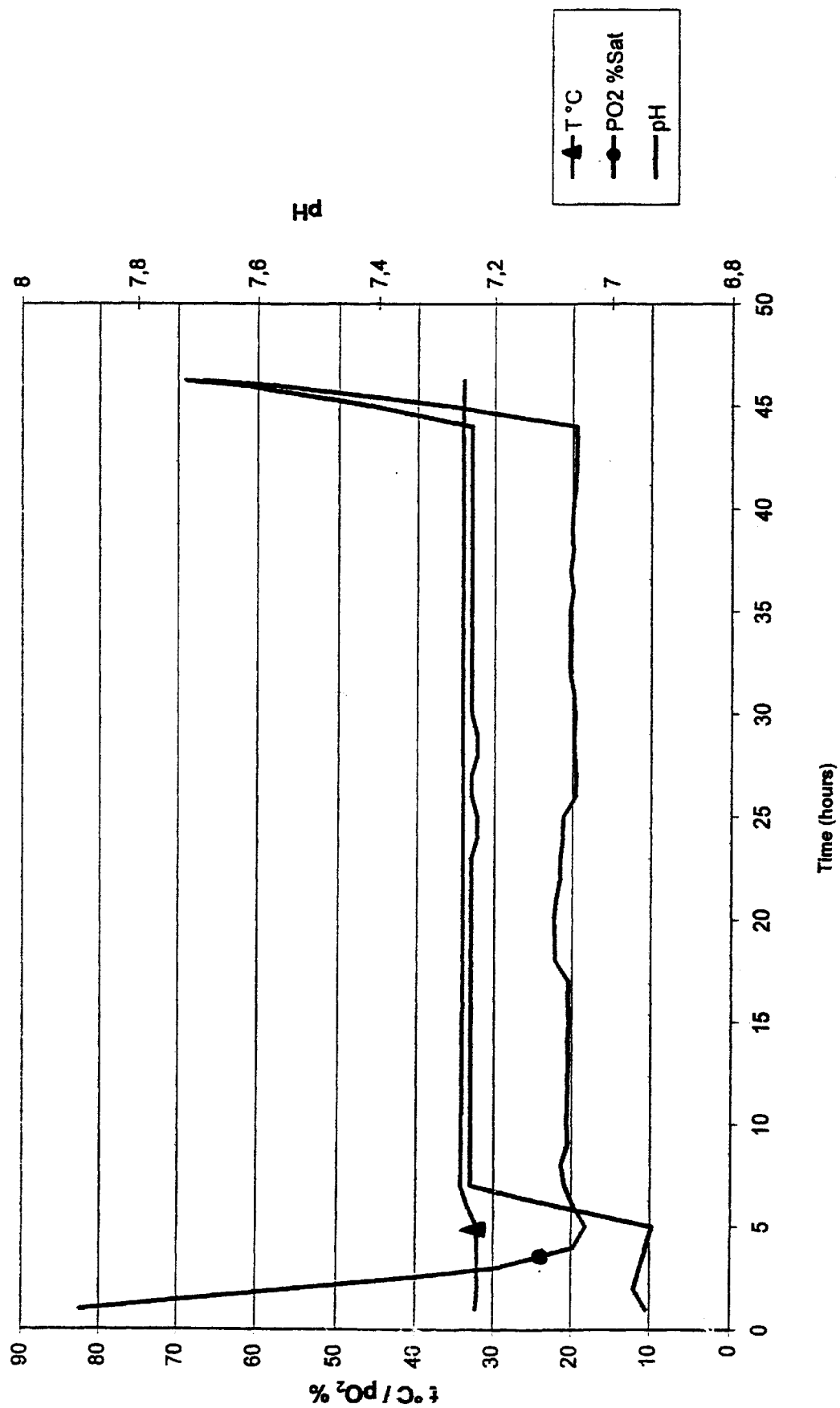
FIG. 7 shows the conditions of temperature, dissolved oxygen and pH during the fermentation of strain ATCC 21513 by the process according to the state of the art (sucrose >5 g/l) in Example 7.
Figure 8:
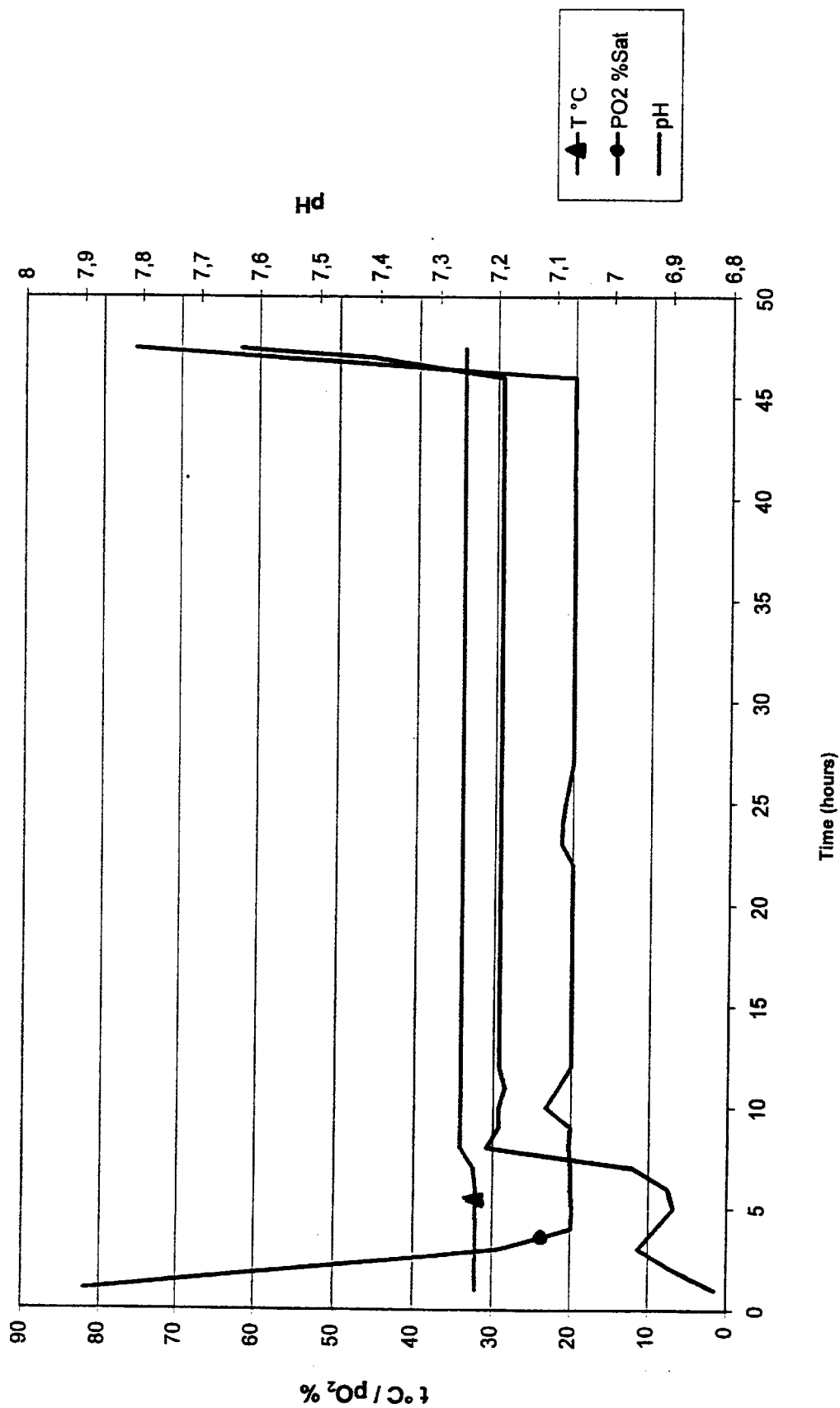
FIG. 8 shows the conditions of temperature, dissolved oxygen and pH during the fermentation of strain ATCC 21253 by the process of the invention in Example 7.
Figure 9:
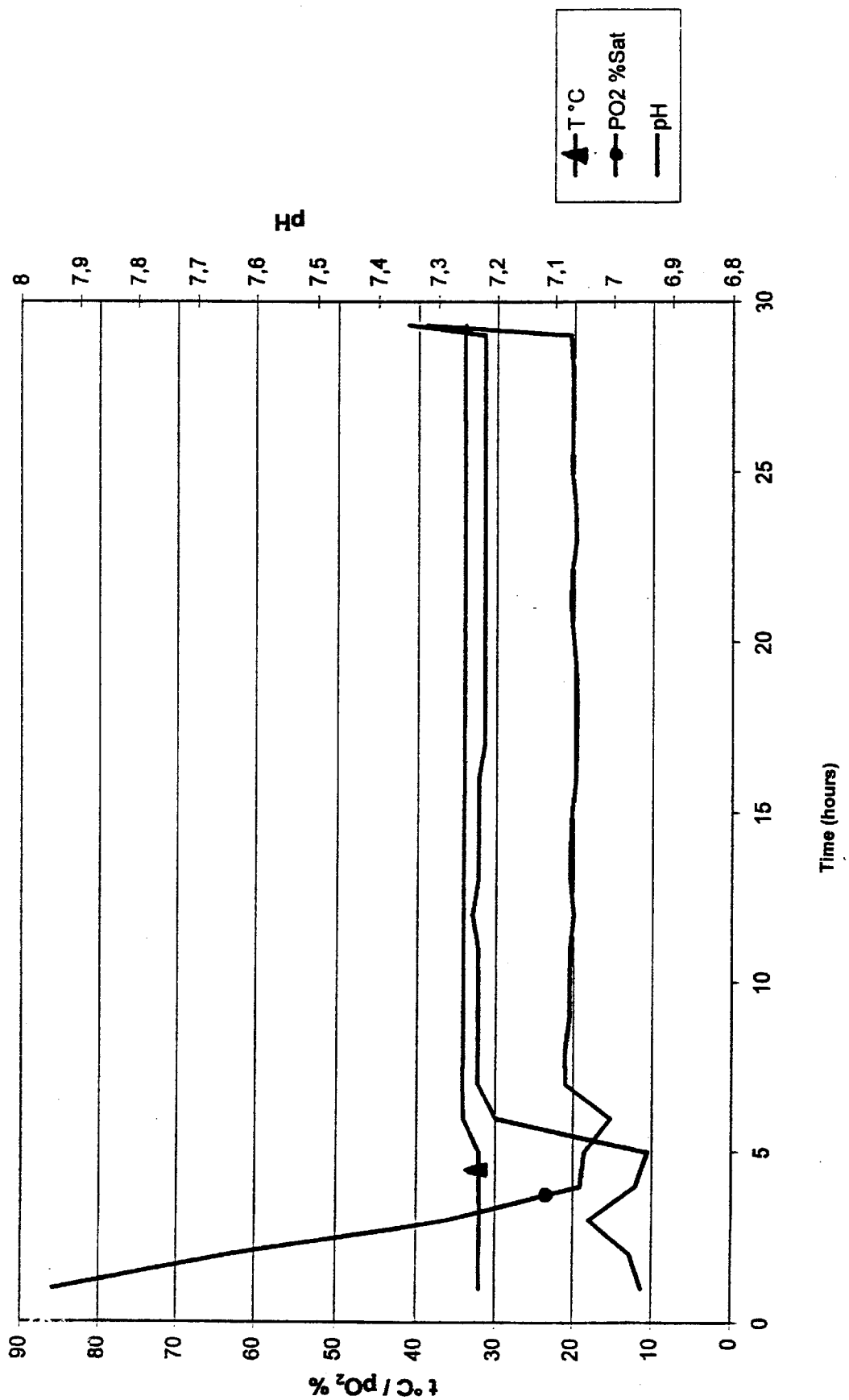
FIG. 9 shows the conditions of temperature, dissolved oxygen and pH during the fermentation of strain ATCC 21253 by the process of the state of the art (sucrose >5 g/l) in Example 7.
Figure 10:
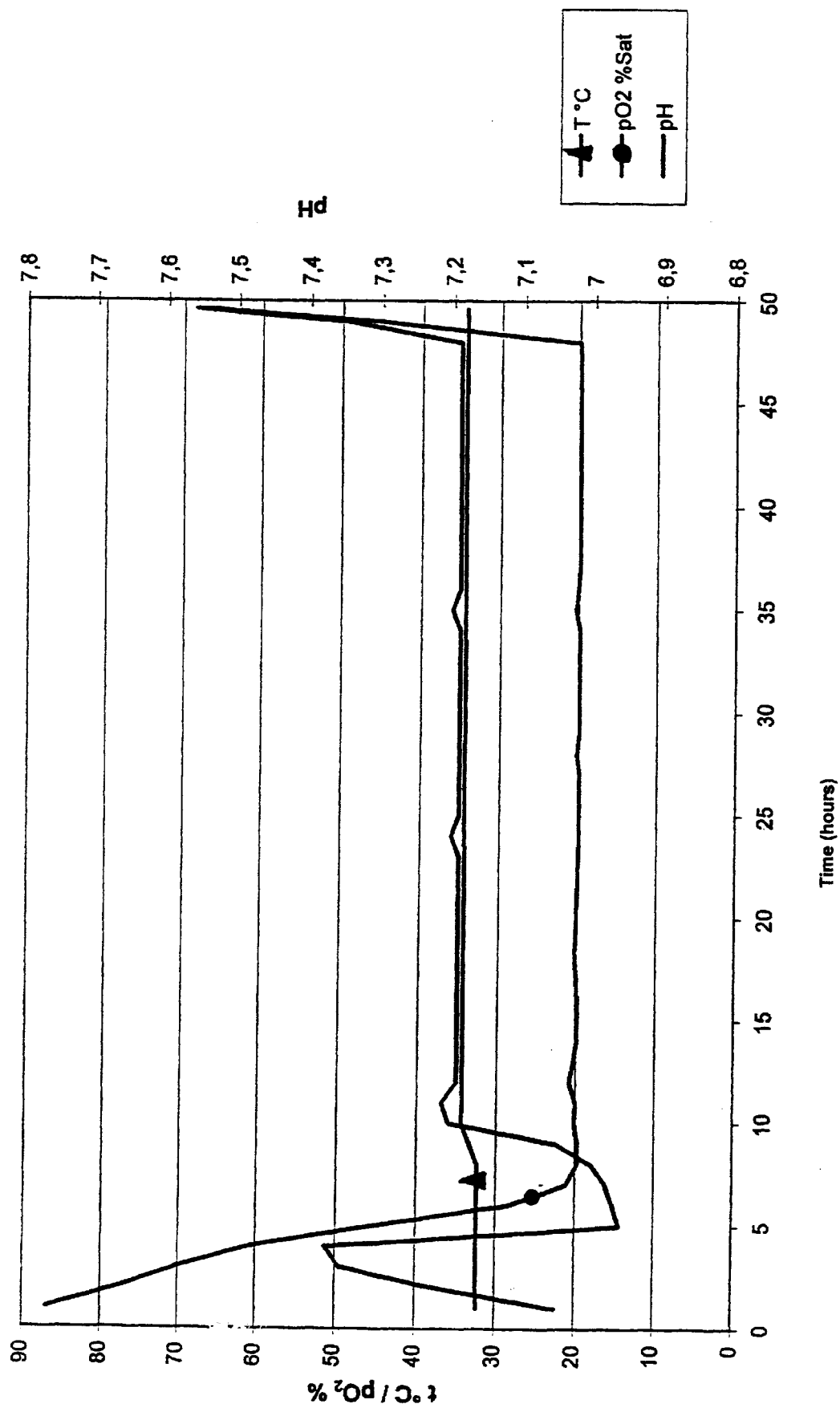
FIG. 10 shows the conditions of temperature, dissolved oxygen and pH during the fermentation of strain ATCC 21544 by the process of the invention in Example 7.
Figure 11:
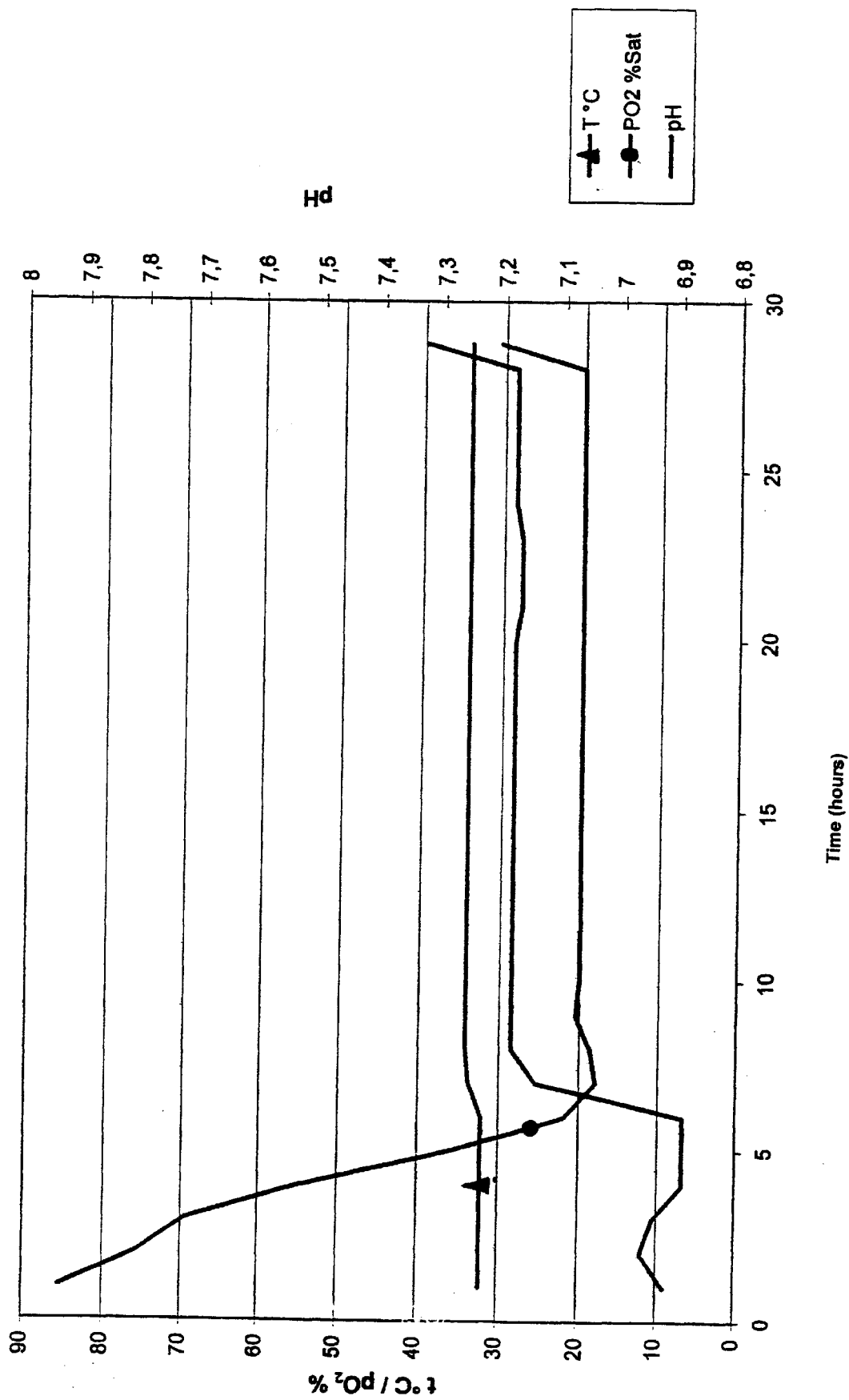
FIG. 11 shows the conditions of temperature, dissolved oxygen and pH during the fermentation of strain ATCC 21544 by the process of the state of the art (sucrose >5 g/l) in Example 7.
Figure 12:
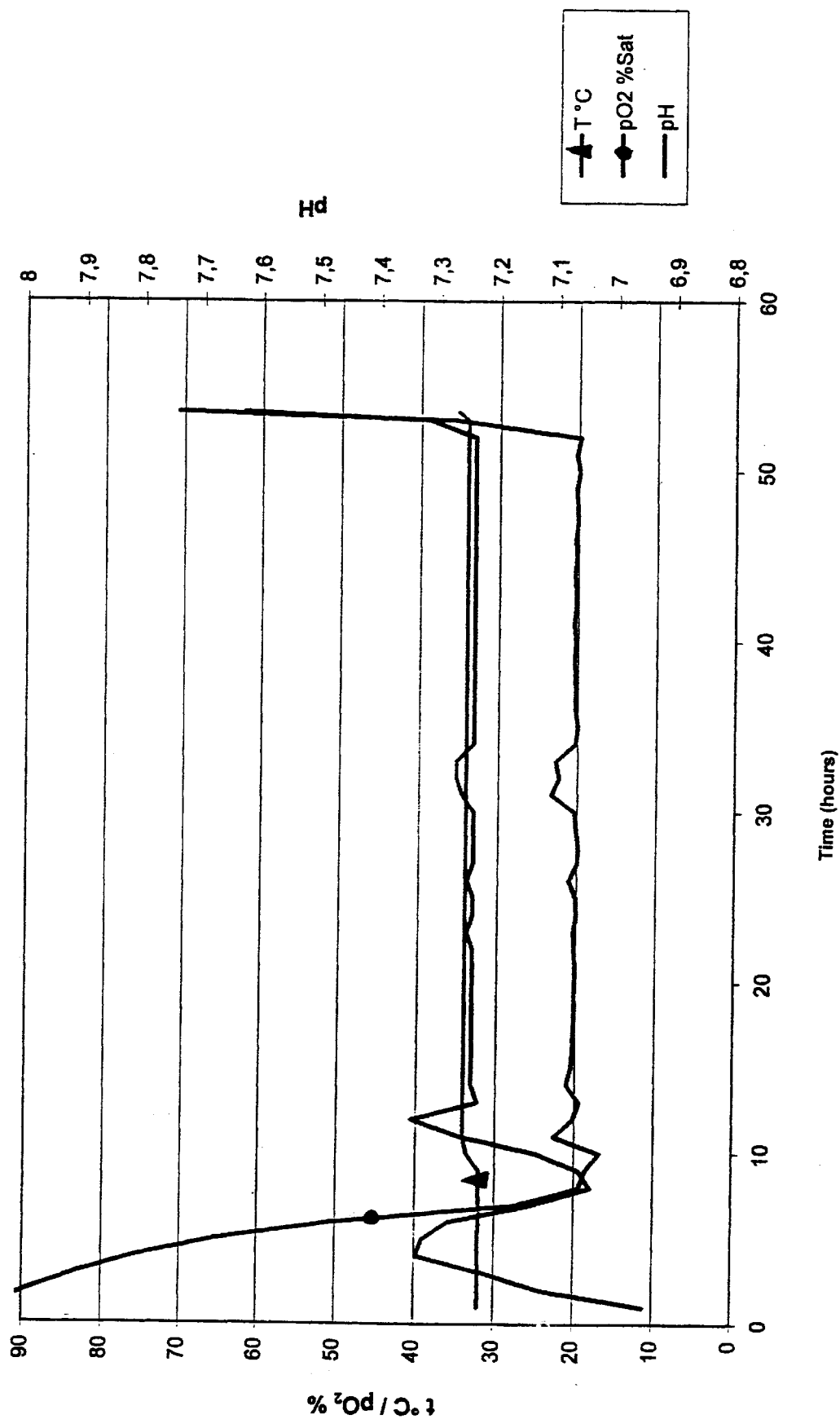
FIG. 12 shows the conditions of temperature, dissolved oxygen and pH during the fermentation of strain ATCC 21543 by the process of the invention in Example 7.
Figure 13:
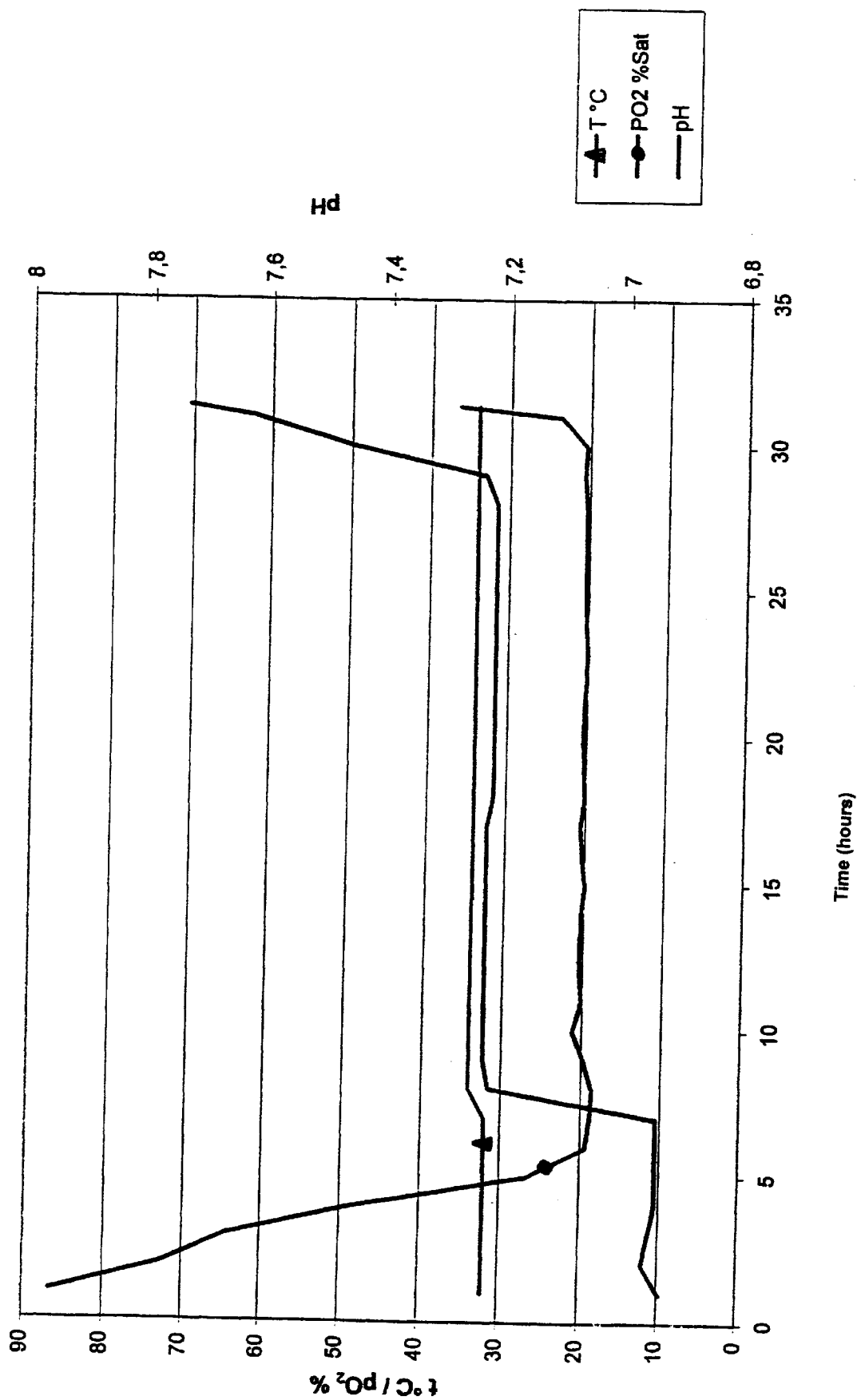
FIG. 13 shows the conditions of temperature, dissolved oxygen and pH during the fermentation of strain ATCC 21543 by the process of the state of the art (sucrose >5 g/l) in Example 7.
Figure 14:
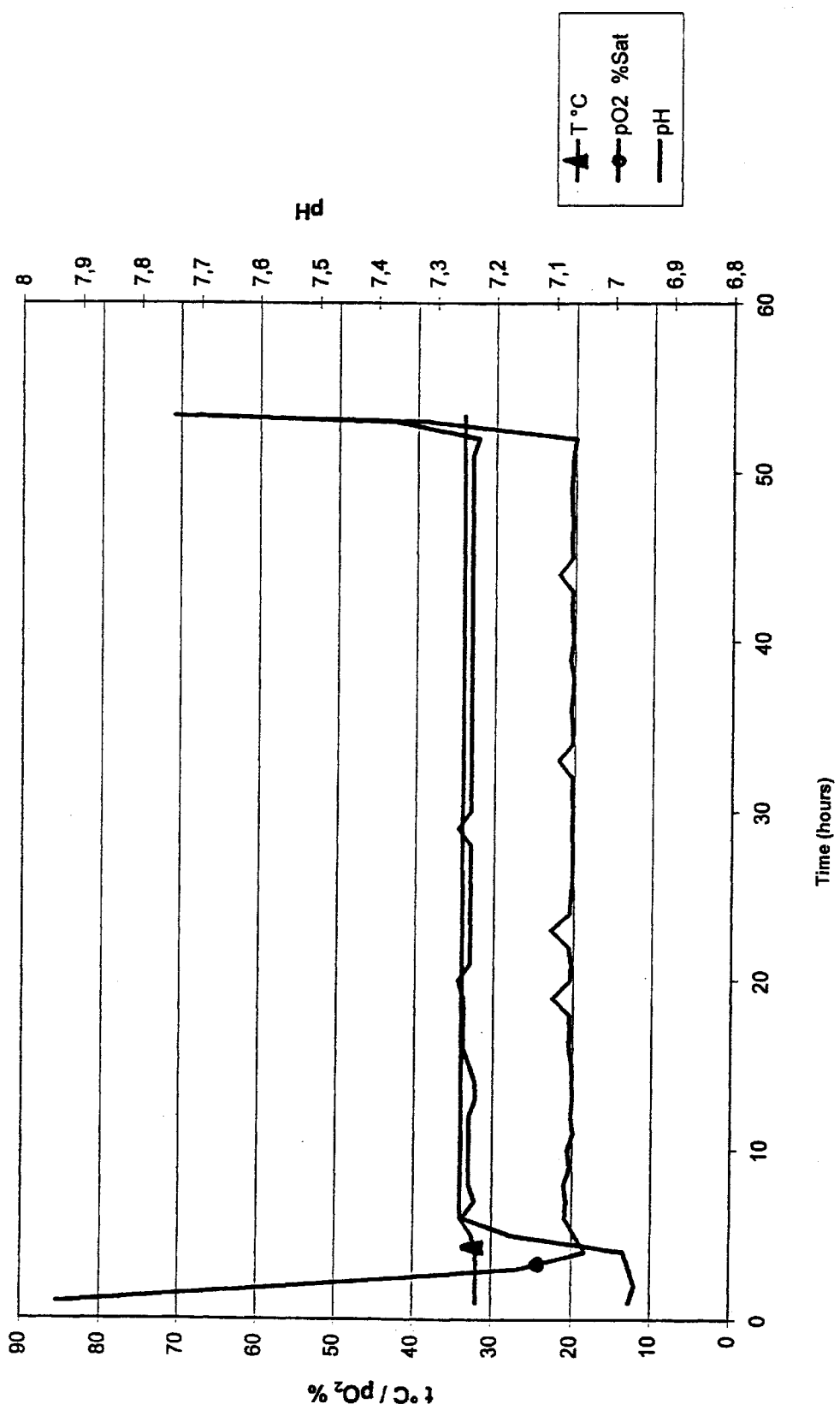
FIG. 14 shows the conditions of temperature, dissolved oxygen and pH during the fermentation of strain ATCC 21527 by the process of the invention in Example 7.
Figure 15:
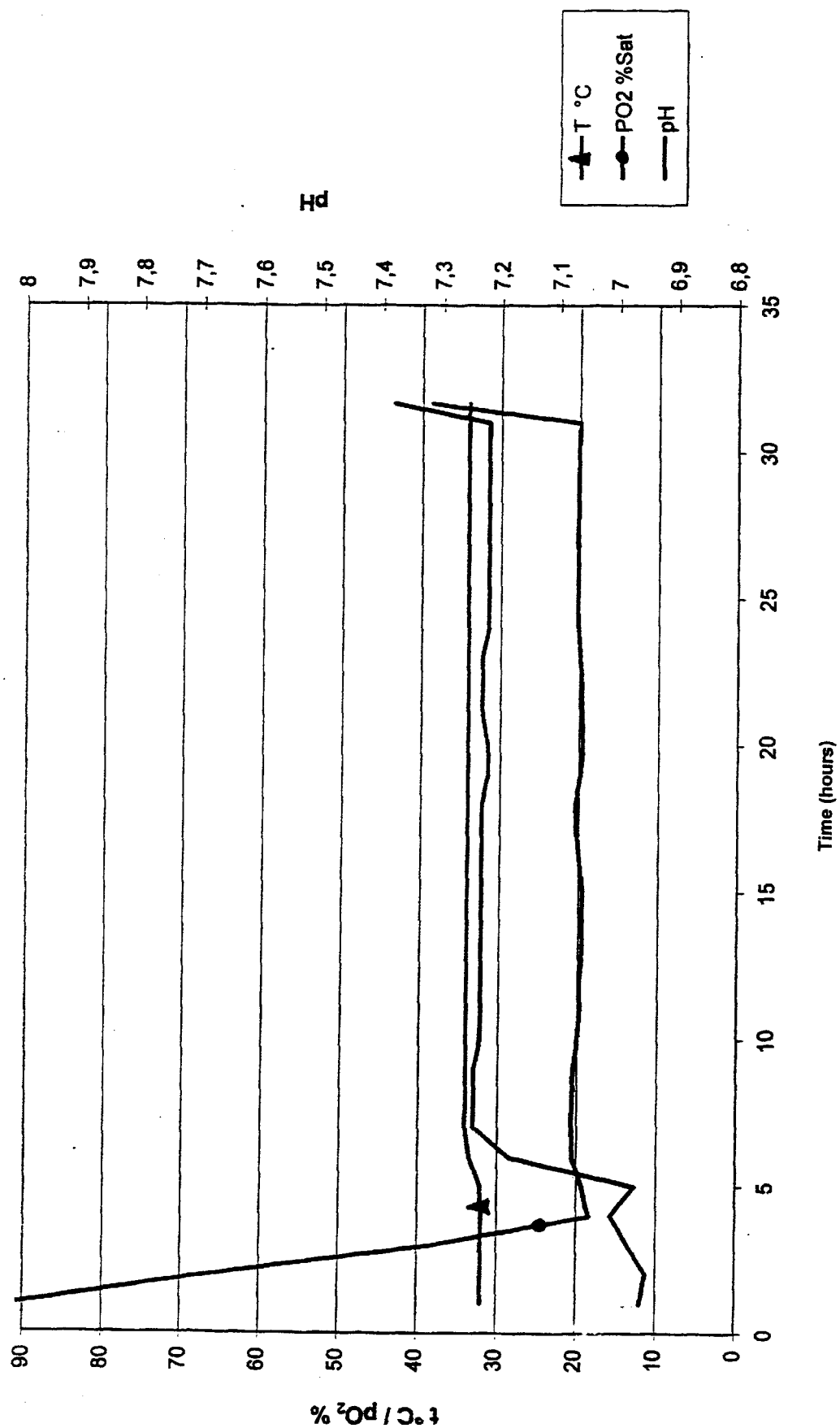
FIG. 15 shows the conditions of temperature, dissolved oxygen and pH during the fermentation of strain ATCC 21527 by the process of the state of the art (sucrose >5 g/l) n in Example 7.
Figure 16:
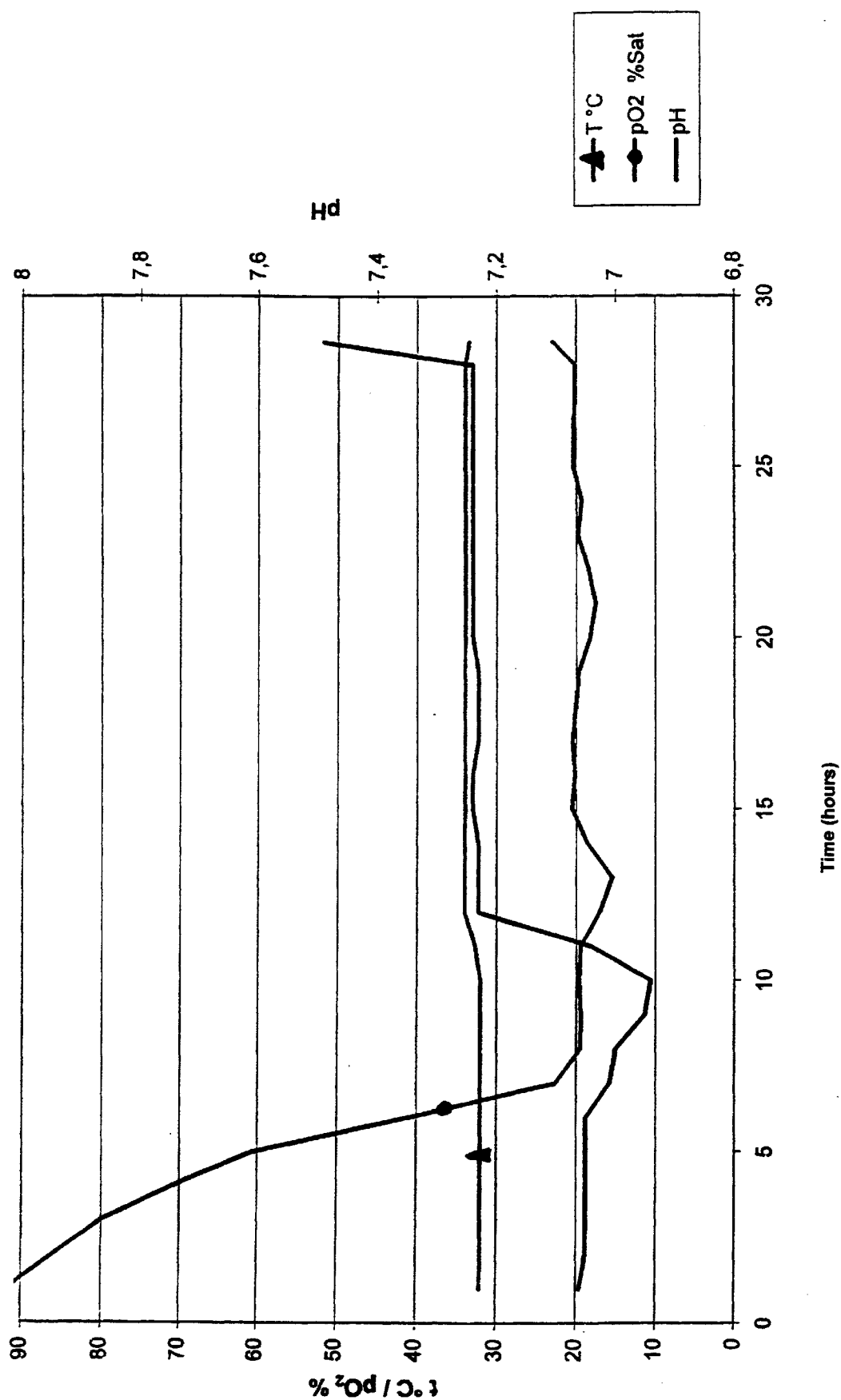
FIG. 16 shows the conditions of temperature, dissolved oxygen and pH during the fermentation of strain DSM 11831 by the process of the invention in Example 8.
Figure 17:
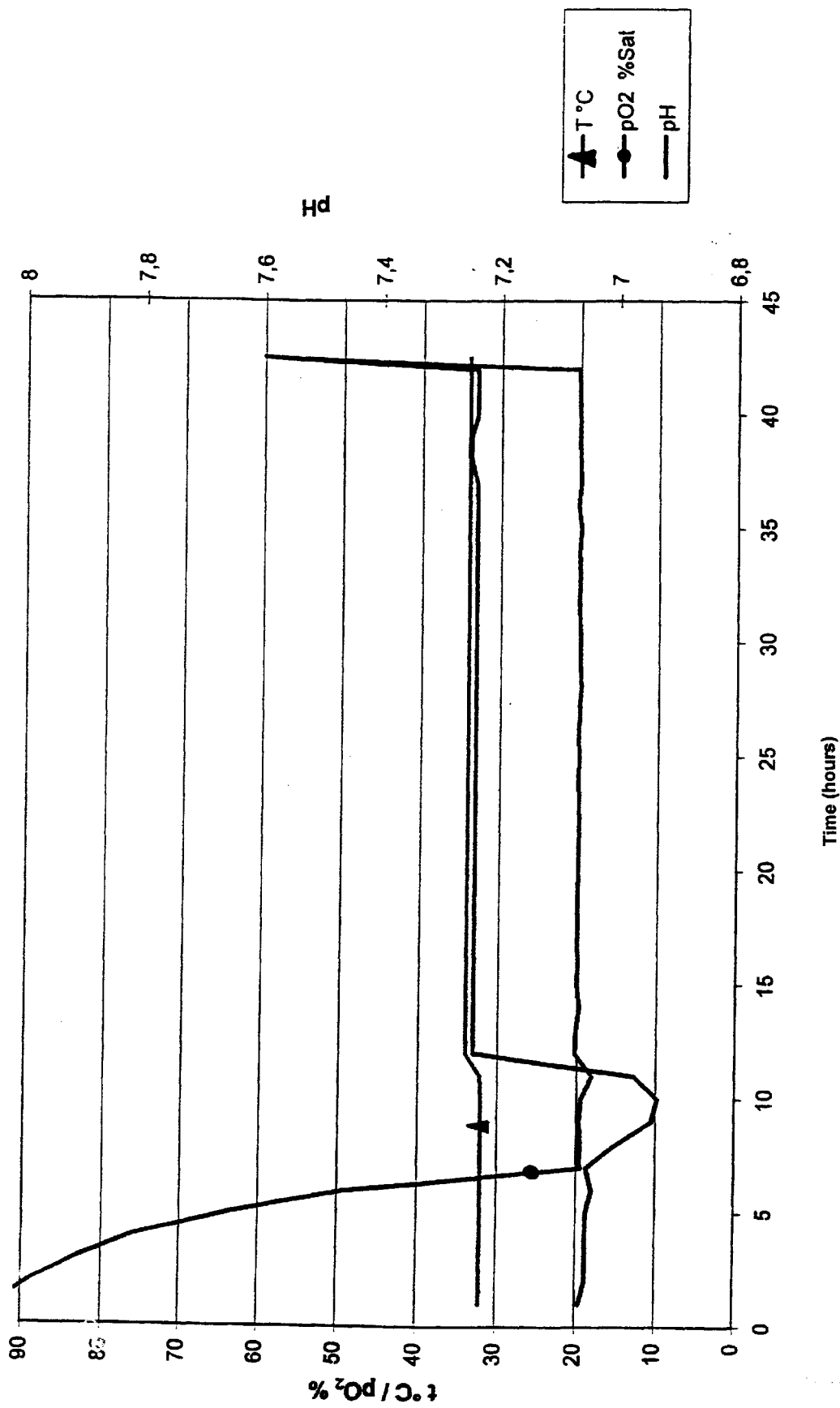
FIG. 17 shows the conditions of temperature, dissolved oxygen and pH during the fermentation of strain DSM 11831 by the process of the state of the art (sucrose >5 g/l) in Example 8.

In addition to containing sources of carbon such as assimilable sugars, sucrose, glucose, molasses or starch hydrolysates and ammonium ions, in the case of autotrophic producers the medium contains complex components as a source of organic supplements (required due to one or more auxotrophies), such as protein hydrolysates as sources of α-aminonitrogen, vitamins and inorganic salts. The vigorous growth at the beginning of fermentation is generally a logarithmic growth phase. This may be shortened if required by limiting the supplements and/or the source of carbon until the desired optical density is reached.

The logarithmic growth phase is followed by cell growth, but the extent of this growth is confined to a small fraction of the vigorous growth phase. Strains producing L-lysine and/or L-threonine are preferably used. The fermentation medium is chosen so that the pH is from 6 to 8, preferably from 7 to 7.5, and the ammonium concentration is from 0.5 to 8 g/l; and the temperature is from 25 to 40° C., preferably from 30 to 36° C. The broth is stirred and as usual amply supplied with oxygen. Metabolization of the sugar may be controlled by the quantity of amino acid added, especially in the case of amino acid-auxotrophic lysine secretors. The concentration of these amino acid supplements or of other necessary supplements after the growth phase is advantageously from 0 to 0.1 g/l each, in particular from 0 to 0.05 g/l each. Thus, for example, in a leucine-auxotrophic lysine secretor, the sugar/leucine ratio in a continuously added feed medium is chosen so that the formation of biomass is limited by the supply of leucine, but at the same time the amount of sugar provided is only a fraction of that which could be converted at the given leucine concentration.

The concentration of utilizable sugars after the vigorous growth phase is advantageously from 0 to <3 g/l, in particular from 0 to 1 g/l. The concentration of 0 g/l in the fermentation broth does not mean, either with respect to any supplements required or with respect to the source of carbon, that these substances are not supplied continuously. It means that these compounds are supplied in a quantity which is immediately taken up by the bacterial cultures.

This fermentation carried out by the processor according to the invention has numerous very important advantages compared with the conventional processes mentioned above, namely:

1. The metabolic activity and hence the oxygen requirement and the evolution of heat of the culture can be influenced directly and without delay by the rate of supply of feed and adapted to the capacity of the fermenter.

2. The fermentation broths are distinguished by a higher product content of the dry mass as a whole and hence greater purity. Loss by the formation of by-products is prevented by the fact that over the whole period of feeding, the bacterial culture is offered less substrate than it would be capable of converting, so that the source of carbon constitutes the primary limitation (contrary to the prior art).

3. The fermentations have a higher yield than fermentations in which limitation is primarily by way of supplements.

4. In the process of monitoring the product, fermentation can be stopped directly and without any time lag at an optimum or at a plateau, and the gross yield is at all times equal to the net yield.

5. In a working up project which includes direct concentration of the fermentation broth by evaporation, the fermenter contents can be immediately used for working up in the event of technical breakdown without the quality of the product being impaired by a high residual sugar content.

No special process to select appropriate strains is needed.

The claimed fermentative preparation is suitable for all amino acid secreting strains of the genus Brevibacterium or Corynebacterium.

Aspartokinase insensitivity for feedback inhibition to lysine and threonine ($Ak^{fbr}$) and reduced homoserine dehydrogenase activity (so-called leaky-type: $HDH^{leaky}$) are basic features of a prototrophic lysine producer (Hilliger & Hertel, J. Basic Microbiol, 37 1, 29–40, 1997; EP 0 754 756). Additionally present may be a reduced homoserine kinase (HK) activity. These markers are present in, for example, the model lysine-producing strain DM 708 (DSM 11831).

The process according to the invention has been found to work with lysine producers of the species Corynebacterium glutamicum. In particular, strains of Corynebacterium glutamicum with the following phenotypes are applicable:

leu$^-$, AEC$^r$+additional markers hse$^-$, AEC$^r$+additional markers $HDH^{leaky}$, AEC$^r$+additional markers $HDH^{leaky}$, $HK^{leaky}$, AEC$^r$+additional markers.

The process according to the invention is therefore applicable to protrophic and auxotrophic strains of lysine producers.

The Examples which follow illustrate specific embodiments of the process according to the invention and show that optional strains excrete higher amounts of amino acids when used in the method of the invention in comparison with the state-of-the-art.

EXAMPLES

Example 1 (Comparative Example)

5.1 kg of a sterile solution containing the components of Table 1 were introduced into a fermentation container equipped with stirrer and ventilation system:

TABLE 1

| Medium 1 | |
|---|---|
| Water | 4540 g |
| Molasses | 26 g |
| Glucose | 125 g |
| Corn gluten hydrolysate (hydrolyzed with sulfuric acid) | 35 g |
| Hydrolysate of the producer biomass (hydrolyzed with sulfuric acid) | 320 g |
| Ammonium sulphate | 45 g |
| Phosphoric acid 85% | 7 g |
| Magnesium sulphate, other mineral salts, traces and biotin and thiamine | 3 g |

The solution was adjusted to pH 7.3 with ammonia solution. 0.6 l of an inoculum of a Corynebacterium glutamicum DM 346-1 carrying the genetic markers leu$^-$, oxalysine resistance and aminoethyl resistance were added to this solution at 33 to 35° C. The inoculum had been prepared by incubation for 15 hours at 33° C. and pH 7 with stirring and ventilation in a medium containing 4.4 mass percent of molasses in addition to 2% of sucrose and 14% of soya bean meal hydrolysate (hydrolyzed with sulfuric acid) with the addition of 3% of ammonium sulphate, 0.05% of phosphoric acid and 0.02% of magnesium sulphate and the vitamins, biotin and thiamine.

With vigorous stirring, ventilation and adjustment of the pH to about 7.3 by means of aqueous ammonia solution, the medium described in Table 2, neutralized with aqueous ammonia solution was continuously added in the conventional manner within 32 hours after termination of the logarithmic growth phase in the main fermenter so that the measurable sugar concentration in the fermentation broth was from 5 to 35 g/l (enzymatic determination based on sucrose and glucose).

TABLE 2

| Medium 2 | |
|---|---|
| Water | 1250 g |
| Molasses | 94 g |
| Glucose | 1465 g |
| Corn gluten hydrolysate (sulfuric acid) | 39 g |
| Hydrolysate of the producer biomass (sulfuric acid) | 265 g |
| Ammonium sulphate | 31 g |
| Phosphoric acid 85% | 4 g |
| Magnesium sulphate, other mineral salts, traces and biotin and thiamine | 2 g |

At the end point of fermentation when all the assimilable sugar in the fermentation medium had been used up, the degree of conversion of sugar into lysine was 35%, calculated as lysine hydrochloride, and the lysine base content of the concentrated fermentation solution free from biomass was 45%.

Example 2

Preparation of the inoculum, the medium introduced into the main fermenter and the culture conditions are similar to those of Example 1.

Medium 2 also has the same composition as in Table 2 with the exception of the modifications listed in Table 3.

TABLE 3

Modifications of Medium 2 for Example 2

| | |
|---|---|
| Water | 1560 g |
| Molasses | 75 g |
| Glucose | 1170 g |

In this experiment, the feed medium was added at the same rate as in Example 1. Analyses of the process based on assimilable sugar showed that, in accordance with the present invention, the measurable concentration of assimilable sugars remained <3 g/l during the entire feed time and was almost always kept <1 g/l. Analyses based on leucine in the fermentation broth, using amino acid analyzer, showed that after the quantity of leucine provided in medium 1 had been used up, the leucine concentration during the feed time was at no point greater than 0.05 g/l.

Unexpectedly, after termination of the fermentation, the degree of conversion of sugar into lysine (calculated as lysine hydrochloride) was 40% and the lysine base content of the concentrated fermentation broth free from biomass was 54%.

Example 3

3980 kg of a sterile medium having the composition in Table 4 was introduced into a 10 m³ reactor:

TABLE 4

Medium 3

| | |
|---|---|
| Sucrose | 320 kg |
| Molasses | 20 kg |
| Corn gluten hydrolysate | 320 kg |
| 25% aqueous ammonium sulphate | 150 kg |
| Citric acid · $H_2O$ | 2.3 kg |
| Phosphoric acid (89%) | 6.6 kg |
| $MgSO_4 \cdot 7H_2O$ | 2.8 kg |
| $CaCl_2 \cdot 2H_2O$ | 75 kg |
| $FeSO_4 \cdot H_2O$ | 113 kg |
| $MnSO_4 \cdot H_2O$ | 113 kg |
| $ZnSO_4 \cdot 7H_2O$ | 5.6 g |
| $CuSO_4 \cdot 5H_2O$ | 0.6 g |
| Biotin | 1.1 g |
| Thiamine · HCl | 0.8 g |
| $NH_4OH$ (2–3%) | 1010 kg |
| Water | 2258 kg | pH: 7.0

The contents of the reactor are stirred at 33° C. and vigorously ventilated. After the transfer of 250 l of inoculum of the strain DM 282-2 carrying the genetic markers leucine auxotrophic and aminoethylcysteine resistant (after incubation for 16 hours in a medium containing 6% of molasses, 14% of soya bean meal hydrolysate, 1% of ammonium sulphate and 0.1% of phosphoric acid at pH 7 and 30° C.) into a 10 mm³ reactor, the pH was maintained at 7.0 by means of aqueous ammonia and the rate of ventilation was adjusted so that the dissolved oxygen content was always about 15% saturation.

After the culture had grown to an optical density (535 nm) of about 30, a production medium (medium 4) having the composition in Table 5 was added at the rate of 30 l/h:

TABLE 5

Production Medium 4

| | |
|---|---|
| Sucrose | 940 kg |
| Molasses | 50 kg |
| Corn gluten hydrolysate | 180 kg |
| 25% aqueous ammonium sulphate | 80 kg |
| Citric acid · $H_2O$ | 1 kg |
| Phosphoric acid (89%) | 2.8 kg |
| $MgSO_4 \cdot H_2O$ | 1.2 kg |
| $FeSO_4 \cdot H_2O$ | 48 kg |
| $MnSO_4 \cdot H_2O$ | 48 kg |
| $ZnSO_4 \cdot 7H_2O$ | 2.4 g |
| $CuSO_4 \cdot 5H_2O$ | 0.3 g |
| Biotin | 0.6 g |
| Thiamine · HCl | 0.4 |
| $NH_4OH$ (2–3%) | 80 kg |
| Water | 740 kg | pH: 7.5

The pH was maintained at 7.3 during the production phase. In accordance with the present invention, a concentration of assimilable sugar of 1 g/l was not exceeded during the feed phase after the sugar provided in the growth medium had been used up, and the measurable leucine concentration was <0.05 g/l. Unexpectedly, at the end of fermentation, the degree of conversion of sugar into lysine (in the form of lysine hydrochloride) was 32.3% and the lysine base content of the concentrated fermentation broth free from biomass was 54.7%.

Example 4 (Comparative Example)

Preparation of the inoculum, the process parameters and the media in the growth phase and in the production phase correspond to the conditions indicated in Example 3 although feeding was in this case carried out at a rate of about 100 l/h. As a result, the measurable concentrations of assimilable sugar during the feeding period after the sugar provided in the growth medium had been used up were always distinctly about 5 g/l, but the concentration of leucine remained <0.05 g/l. The degree of conversion of sugar into lysine (calculated as lysine hydrochloride) was 30.9% at the end of fermentation, and the lysine base content of the fermentation broth free from biomass was 43.5%

Example 5 (Comparative Example)

The media for culture, growth and production are similar in composition to the media of Example 1 except that the glucose was replaced by 25 g/l of sucrose in the growth medium and by 564 g/l of sucrose in the production medium. The incubation parameters including preparation of the inoculum are also identical. 0.82 kg (0.8 l) of sterile growth medium were introduced into a small fermenter equipped with stirrer and ventilating means. To this solution were added 1.1 l of an inoculum of *Corynebacterium glutamicum* DSM 5715[1] at 33 to 35° C. When an optical density of about 30 (535 nm) had been reached, 533 g (420 ml) of production medium were continuously added within 24 hours.

[1] Deposited into the Deutsche Sammlung von Mikroorganismen und Zellkulturen (DSM), Mascheroder Weg 1B, D-38124 Braunschweig, Germany, on Dec. 19, 1989 under accession number DSM 5715.

During the time of feeding, the measurable sugar content was always about 5 g/l in the fermentation medium and the leucine content after the quantity provided in the growth medium had been used up was always <0.05 g/l.

At the end of fermentation, 74 g of lysine were detected in the medium as lysine hydrochloride, which in the case of a total input of sucrose of 275 g corresponds to a degree of conversion of 27%. The lysine content of the total dry biomass was 30.5%.

Example 6

In another experiment also using strain DSM 5715, in which all the parameters of media and incubation were identical to those of Example 5, the production medium was continuously fed in within 39 hours. In accordance with the present invention, the actual sucrose concentration during the feed period after the source of C and leucine provided in the growth medium had been used up was <1 g/l and the leucine concentration was <0.5 g/l. Unexpectedly, at the end of fermentation, 89 g of lysine (in the form of lysine hydrochloride) were detected in the medium, and the degree of conversion was 32%. The lysine base content in the total dry mass was 36.3%.

Example 7

As a further demonstration of the applicability of the process of the invention to all strains of *Cornyebacterium glutamicum*, the following strains were used in two comparative tests. Each strain was tested for lysine production yield produced under conditions used in the current state of the technology and under the process according to the invention:

(1) ATCC 13286 (U.S. Pat. No. 2,979,439)
(2) ATCC 21513 (U.S. Pat. No. 3,687,810)
(3) ATCC 21515 (U.S. Pat. No. 3,687,810)
(4) ATCC 21253 (U.S. Pat. No. 3,708,395)
(5) ATCC 21543 (U.S. Pat. No. 3,708,395)
(6) ATCC 21544 (U.S. Pat. No. 3,708,395)
(7) ATCC 21527 (U.S. Pat. No. 3,708,395)

The strains were all cultured by the following procedure:

Three slants (Casein peptone/trypticase soy agar) were inoculated with each microorganism. They were incubated for 48 hours at 30° C.

After incubation, the slants were suspended with 3 ml sterile physiological sodium chloride solution. Then the suspensions were transferred to 2-liter shaker flasks containing 300 ml of autoclaved Medium A1-86 (Table 6).

Only sugar beet molasses were used in these studies. The European grades contain 48–52% sucrose. The sucrose content of the molasses is usually determined before use. For these studies, the molasses was determined to contain 49.44% sucrose.

The shaker flasks were then incubated on a rotary shaker at 150 rpm for 24 hours at 30° C.

TABLE 6

Medium A1-86

| Components | Medium A1-86 [g/kg] |
|---|---|
| Sucrose | 20.0 |
| Molasses (49.44% sucrose) | 43.60 |
| SMH (soybean meal hydrolysate) | 138.0 |
| Yeast extract | 0.50 |
| Ammonium sulfate | 32.0 |
| Urea | 6.0 |
| Citric acid monohydrate | 0.60 |
| $KH_2PO_4$ | 0.50 |
| $MgSO_4 \cdot 7H_2O$ | 0.25 |
| $MnSO_4 \cdot H_2O$ | 0.010 |
| $FeSO_4 \cdot 7H_2O$ | 0.010 |
| $CaCO_3$ | 1.60 |

TABLE 6-continued

Medium A1-86

| Components | Medium A1-86 [g/kg] |
|---|---|
| L-leucine | 0.0596 |
| L-threonine | 0.2436 |
| L-methionine | 0.3292 |
| Biotin | 0.0040 |
| Thiamine hydrochloride | 0.0020 |
| Struktol (antifoam agent) | 0.8 | pH adjusted with 25% NaOH to 7.0

The contents of the 3 shaker flasks were combined to make the inoculum.

A 15-liter reactor containing Medium M1-257, which had been prepared as follows, was then inoculated with 740 g of this inoculum.

The medium components of Table 7 were weighed out and made up with water to 4.5 kg. The pH was adjusted to 7 with ammonium hydroxide solution. Water was added to make 5.2 kg, and the nutrient was placed in the fermentor. Sterilization was done at 121° C. for 60 minutes. The final volume was 4.2 kg (decrease on sterilization due to loss of condensate). The temperature was maintained at 32° C., the pH was adjusted to 7 with ammonium hydroxide solution, and the fermentor was aerated at 4.5 liters/minute at a pressure of 0.5 bar.

TABLE 7

| | Medium M1-257 | |
|---|---|---|
| Components | Medium 1 M1-257 [g] | Final concentration for 4.2 kg after sterilization [g/kg] |
| Sucrose | 124.8 | 29.7 |
| Molasses (49.44% sucrose) | 124.8 | 29.7 |
| MKH (corn gluten hydrolysate) | 296.4 | 70.6 |
| Ammonium sulfate | 52.0 | 12.4 |
| Citric acid monohydrate | 3.12 | 0.7 |
| $H_3PO_4$ 85% | 9.1 | 2.2 |
| $MgSO_4 \cdot 7H_2O$ | 3.9 | 0.93 |
| $MnSO_4 \cdot H_2O$ | 0.16 | 0.038 |
| $ZnSO_4 \cdot 7 H_2O$ | 0.008 | 0.002 |
| $FeSO_4 \cdot 7 H_2O$ | 0.16 | 0.038 |
| L-threonine | 2.3 | 0.55 |
| L-methionine | 2.5 | 0.60 |
| Biotin | 0.0026 | 0.0006 |
| Thiamine hydrochloride | 0.001 | 0.00024 |
| Struktol (antifoam agent) | 3.1 | 0.74 |

After inoculation the pH was controlled at pH 7 (with ammonium hydroxide solution) until beginning of nutrient addition, and thereafter at pH 7.3. The dissolved oxygen content was maintained at 20% by the stirrer speed and by aeration. A batch feeding medium (M2-184) was prepared for supplying supplements during the fermentation period. Medium M2-184 was prepared with the composition in Table 8.

TABLE 8

Medium M2-184 (Total 950 g)

| Components | M2-184 [g/kg] |
|---|---|
| MKH (corn gluten hydrolysate) | 300.5 |
| Ammonium sulfate | 33.7 |
| Citric acid monohydrate | 1.7 |
| $MgSO_4 \cdot 7H_2O$ | 2.10 |
| $MnSO_4 \cdot 7H_2O$ | 0.084 |
| $FeSO_4 \cdot 7H_2O$ | 0.084 |
| L-threonine | 2.46 |
| L-methionine | 2.64 |
| Biotin | 0.00084 |
| Thiamine hydrochloride | 0.00053 | pH adjusted to 7.0 before sterilization with $NH_4OH$ or $H_2SO_4$

The supplement medium M2-184 was added with the feed profile of Table 9 in each experiment.

TABLE 9

Feed profile of medium M2-184

| Feed Step | Time [h] | Feed rate [g/h] | Amount/Step [g] | Total [g] |
|---|---|---|---|---|
| 1 | 5 | 27 | 135 | 135 |
| 2 | 8 | 34 | 272 | 407 |
| 3 | 8 | 40 | 320 | 727 |
| 4 | 5 | 44 | 220 | 947 |

This feed profile for supplement medium M2-184 was identical for the conditions used in the experiments conducted using the current state of the technology and by the process according to the invention.

Sucrose was added as the carbon source in a second feed line with medium M2-114 (Table 10). Medium M2-114 contains 1500 g sucrose in a total quantity of 2650 g resulting in a sucrose concentration of 566 g/kg.

TABLE 10

Medium M2-114

| Component | [g/kg] | Total Amount of Sucrose [g] | Total Amount of Medium [g] |
|---|---|---|---|
| Sucrose | 566 | 1500 | 2650 |

This sucrose containing medium M2-114 was then fed differently under the conditions used in the current state of the technology and for the process according to the invention.

In the experiments done according to the state of the technology, medium M2-114 was added in such a manner that the measurable residual content in the medium was always greater than 5 g/liter. The sucrose content in the broth was checked frequently, particularly in the strong growth phase, in order to be able to adjust the rate of sucrose feeding to the sugar consumption. Thus each fermentation has its individual feeding profile, which was adjusted to the activity curve of the culture.

In the experiments on the process according to the invention, the sugar was added after the sugar provided in the growth medium had been consumed in such a way that the concentration measurable in the medium was always less than 3 g/liter and was generally measured at 0 g/l.

After the sucrose provided in the first medium (medium M1-257) was used up, the M2-114 medium was fed according to a previously established, distinctly lower, metering profile than in the process according to the state of the technology.

To show the simplicity of the process, two different profiles were established (Tables 11 and 12). Their feed rates differ by 20%:

TABLE 11

Profile 1 for ATCC 21544, ATCC 21253, ATCC 21513, ATCC 21515, and ATCC 13286

| Step | Time [hr] | Feed M2-114 [g/hr] | Feed M2-114 [g/min] | Rate of Sucrose/hr [g/hr] | Total Sucrose Added [g] |
|---|---|---|---|---|---|
| 1 | 3.0 | 44.0 | 0.73 | 24.90 | 75 |
| 2 | 15.0 | 61.8 | 1.03 | 34.98 | 599 |
| 3 | 7.5 | 74.0 | 1.23 | 41.88 | 914 |
| 4 | 13.0 | 79.5 | 1.33 | 44.99 | 1498 |

TABLE 12

Profile 2 for ATCC 21527 and ATCC 21543

| Step | Time [hr] | Feed M2-114 [g/hr] | Feed M2-114 [g/min] | Rate of Sucrose/hr [g/hr] | Total Sucrose Added [g] |
|---|---|---|---|---|---|
| 1 | 3.0 | 35.2 | 0.59 | 19.92 | 60 |
| 2 | 15.0 | 49.44 | 0.82 | 27.98 | 480 |
| 3 | 7.5 | 59.2 | 0.99 | 33.51 | 731 |
| 4 | 21.5 | 63.6 | 1.06 | 36.00 | 1505 |

The sucrose concentration in the culture broth was analyzed only for checking. As the sucrose concentration found was always near 0 g/liter, as desired, the feed rate did not need to be corrected.

The lower feed rates gave distinctly lower sugar consumptions/hour, as the culture is sugar-limited at each feeding time.

FIG. 1 shows the sugar consumption rates of the individual fermentations versus time. Consumption rates for the process of the invention are plotted with heavy lines, with '. . . lim' added in the legend. It is clear in this diagram that the process according to the invention limits the high consumption rates at the beginning of the fermentation and that the sugar consumption follows the quantity of sucrose added.

The data show that the sugar concentration was always near zero in the process according to the invention after the sugar was consumed.

TABLE 13

Summary of the experimental fermentations.

| | State of the technology: Sucrose always >5 g/l | Process according to the invention |
|---|---|---|
| ATCC 13286 | | |
| Final conc. of Lys · HCL | 42.5 g/liter | 56.6 g/liter |
| Lys · HCl / Sucrose | 18.6% | 25.8% |
| Lys · HCl / dry weight | 31% | 41% |

TABLE 13-continued

Summary of the experimental fermentations.

| | State of the technology: Sucrose always >5 g/l | Process according to the invention |
|---|---|---|
| ATCC 21515 | | |
| Final conc. of Lys · HCL | 51.65 g/liter | 60.47 g/l |
| Lys · HCl / Sucrose | 24.2% | 27.7% |
| Lys · HCl / dry weight | 41% | 52% |
| ATCC 21513 | | |
| Final conc. of Lys · HCL | 55.95 g/liter | 74.83 g/liter |
| Lys · HCl / Sucrose | 25.4% | 35.9% |
| Lys · HCl / dry weight | 46% | 67% |
| ATCC 21253 | | |
| Final conc. of Lys · HCL | 46.99 g/liter | 60.31 g/liter |
| Lys · HCl / Sucrose | 22.5% | 30.6% |
| Lys · HCl / dry weight | 35% | 50% |
| ATCC 21544 | | |
| Final conc. of Lys · HCL | 46.72 g/liter | 62.15 g/liter |
| Lys · HCl / Sucrose | 24.4% | 32.4% |
| Lys · HCl / dry weight | 36% | 54% |
| ATCC 21543 | | |
| Final conc. of Lys · HCL | 55.25 g/liter | 60.95 g/liter |
| Lys · HCl / Sucrose | 26.3% | 29.7% |
| Lys · HCl / dry weight | 44% | 59% |
| ATCC 21527 | | |
| Final conc. of Lys · HCL | 45.57 g/liter | 62.11 g/liter |
| Lys · HCl / Sucrose | 22.1% | 30.3% |
| Lys · HCl / dry weight | 35% | 51% |

The fermentations according to the invention are distinguished by higher selectivity. That is, the yield of product/substrate is significantly higher. At the same time, the proportion of lysine to total dry weight is higher.

Example 8

A further illustration of the operation of the process of the invention was performed with a prototrophic *Corynebacterium glutamicum* strain DM 708[2]. The complete phenotype for DSM 11831 is: $AK^{fbr}$, $HDH^{leaky}$, $HK^{leaky}$, $AME^r$ (aspartic acid-β-methylester-resistant).

[2] Deposited into the Deutsche Sammlung von Mikroorganismen und Zellkulturen (DSM), Mascheroder Weg 1B, D-38124 Braunschweig, Germany, on Oct. 28, 1997 under accession number DSM 11831.

The fermentation experiments with DSM 11831 were done in 2.5 liter lab fermenters according to the schedule of the previous runs:

1 set of experiments with sugar always >5 g/l 1 set of experiments with sugar limitation Preparation and incubation of shake flask inoculum A1-86 was identical to previous Example (Example 7)

Inoculum quantity: 0.155 kg

Fermenter start medium (M1-389) and supplement feed medium (now M2-239) were modified according to the prototrophy of DSM 11831 (omission of threonine and methionine). Cultivation parameters were kept identical for the parallel fermentations. There was no overpressure for either fermentation. The quantity of start medium for Example 8 was 0.9 kg.

TABLE 14

Start Medium M1-389 for Example 8.

| Components | Medium 1 M1-389 [g/kg] |
|---|---|
| Sucrose | 24 |
| Molasses (49.44% sucrose) | 24 |
| MKH (corn gluten hydrolysate) | 57 |
| Ammonium sulfate | 10 |
| Citric acid monohydrate | 0.6 |
| $H_3PO_4$ · 85% | 1.75 |
| $MgSO_4$ · $7H_2O$ | 0.75 |
| $MnSO_4$ · $H_2O$ | 0.03 |
| $ZnSO_4$ · $7H_2O$ | 0.0015 |
| $FeSO_4$ · $7H_2O$ | 0.03 |
| Biotin | 0.0005 |
| Thiamine hydrochloride | 0.0002 |
| Struktol (antifoam agent) | 0.6 |

Also the feeding characteristics were kept identical. The supplement feed for DM 708 totaled 0.199 kg.

TABLE 15

Medium M3-239 for Example 8.

| Components | M3-239 [g/kg] |
|---|---|
| MKH (corn gluten hydrolysate) | 300.5 |
| Ammonium sulfate | 33.7 |
| Citric acid monohydrate | 1.7 |
| $MgSO_4$ · $7H_2O$ | 2.10 |
| $MnSO_4$ · $H_2O$ | 0.084 |
| $FeSO_4$ · $7H_2O$ | 0.084 |
| Biotin | 0.00084 |
| Thiamine hydrochloride | 0.00053 |
| pH $NH_4OH$ | 7.0 |

TABLE 16

Feed profile for supplement-medium M3-239:

| Feed Step | Time [h] | Feed Rate [g/h] | Amount/Step [g] | Total [g] |
|---|---|---|---|---|
| 1 | 5 | 5.7 | 28.5 | 28.4 |
| 2 | 8 | 7.1 | 71 | 99.5 |
| 3 | 8 | 8.4 | 67.2 | 166.7 |
| 4 | 5 | 9.2 | 33.3 | 200 |

As in the previous Examples, sucrose was added in a second feed line with medium M2-114. Medium M2-114 contains 315 g sucrose in a total quantity of 556 g resulting in a sucrose concentration of 566 g/kg.

The sucrose medium M2-114 was fed differently under the conditions used in the state of the technology (sugar always >5 g/l) and for the process according to the invention (sugar limitation).

In the experiment done according to the state of the technology, Medium M2-114 was added in such a manner that the measurable residual content in the medium was always greater than 5 g/l. The sucrose content was checked frequently, particularly in the strong growth phase in order to be able to adjust the rate of sucrose feeding to the sugar consumption.

In the experiment according to the process of the invention sugar limitation) the sugar was added after the sugar provided in the growth medium had been consumed in such a way that the concentration measurable in the medium was always less than 3 g/l and was generally at 0 g/l. After the sucrose provided in the M1 (M1-89) was used up, the M2-114 medium was fed according to a previously established, distinctly lower, metering profile than in the process according to the state of the technology (Table 17).

TABLE 17

Metering Profile for the Process of the Invention (Example 8).

| Step | Time [hr] | Feed M2-114 [g/hr] | Feed M2-114 [g/min] | Rate of Sucrose/hr [g/hr] | Total Sucrose Added [g] |
|---|---|---|---|---|---|
| 1 | 3.0 | 12.0 | 0.2 | 6.8 | 20 |
| 2 | 15.0 | 16.9 | 0.28 | 9.6 | 163 |
| 3 | 7.5 | 20.2 | 0.34 | 11.2 | 249 |
| 4 | 13.0 | 21.7 | 0.36 | 12.3 | 315 |

The sucrose concentration in the culture broth was analyzed only for checking. as the sucrose concentration found was always near 0 g/l, as desired, the feed rate did not need to be corrected.

As shown in Table 18, the process according to the invention is distinguished by higher selectivity. That is that the yield is significantly higher. At the same time, the proportion of lysine to total dry weight is higher.

TABLE 18

Comparative Results of Example 8.

|  | State of the technology | Processing according to the invention |
|---|---|---|
| DM 708 |  |  |
| Final conc. of Lys · HCl | 60.5 g/l | 63.8 g/l |
| Lys · HCl/Sucrose | 26.4% | 28.2% |
| Lys · HCl/Dry weight | 45.2% | 47.3% |

Example 9

Other Sources of Carbon for this Process:

Corynebacterium can metabolize glucose, maltose, sucrose, fructose, mixtures of these sugars, molasses and starch hydrolysate.

As an Example of the capability of DSM 11831 to utilize other carbon sources, shake flask fermentations were performed with 57.5 g/l of C-source. The results of the fermentations as the concentration of lysine produced with the corresponding C-source is given in Table 19.

TABLE 19

Lysine Production with Different C-Sources.

| C-Source | Lysine (g/l) | OD |
|---|---|---|
| Sucrose | 15.4 | 13.1 |
| 50% Fructose + 50% Glucose | 15.3 | 18.1 |
| Glucose | 17.7 | 15.8 |
| Fructose | 15.4 | 15.0 |
| 90% Glucose + 10% Maltose | 16.0 | 17.1 |

As is shown in Table 19, the lysine-producing *Corynebacterium glutamicum* is capable of utilizing a variety of carbon sources in producing lysine.

Influence of Process Parameters on Lysine Production with Corynebacterium:

The process of the invention has been checked and was found to be valid under the following conditions:

pH 6.5–7.6 dissolved oxygen: down to a level of dissolved oxygen of 0.5% temperature 29–37° C.

Further variations and modifications of the invention will be done apparent to those skilled in the art from the foregoing and are intended to be encompassed by the claims appended hereto.

German priority application P 41 30 867.0, filed on Sep. 17, 1992, is relied on and incorporated by reference.

We claim:

1. A process for the fermentative preparation of L-lysine, said process comprising;
   a) cultivating an L-lysine producing bacterial strain of the species *Corynebacterium glutamicum* in a nutrient medium containing sugar in order to produce L-lysine, and
   (b) continuously feeding said strain with an amount of sugar sufficient to maintain the sugar concentration in the nutrient medium at a concentration of less than 3 g/l for a time sufficient to accumulate L-lysine in the nutrient medium.

2. The process according to claim 1, wherein a source of said sugar is molasses.

3. The process according to claim 1, wherein the concentration of said sugar is less than 1 g/l.

4. The process according to claim 1, further comprising: isolating said L-lysine.

5. The process according to claim 1, wherein the bacterial strain of the species *Corynebacterium glutamicum* expresses a phenotype comprising a member selected from the group consisting of:
   a) leu$^-$ and AEC$^r$;
   b) hse$^-$ and AEC$^r$;
   c) HDH$^{leaky}$ and AEC$^r$; and,
   d) HDH$^{leaky}$, HK$^{leaky}$ and AEC$^r$.

6. The process according to claim 1, wherein said sugar comprises at least one of sucrose, glucose, maltose and fructose.

7. A process for the fermentative preparation of L-lysine, said process comprising;
   (a) cultivating an L-lysine producing bacterial strain of the species *Corynebacterium glutamicum* in a nutrient medium containing sugar in order to produce L-lysine, and
   (b) maintaining the sugar concentration of the nutrient medium below 3 g/l.

8. The process according to claim 7, wherein a source of said sugar is molasses.

9. The process according to claim 7, wherein the concentration of said sugar is less than 1 g/l.

10. The process according to claim 7, further comprising: isolating said L-lysine.

11. The process according to claim 7, wherein the bacterial strain of the species *Corynebacterium glutamicum* expresses a phenotype comprising a member selected from the group consisting of:
   a) leu$^-$ and AEC$^r$;
   b) hse$^-$ and AEC$^r$;
   c) HDH$^{leaky}$ and AEC$^r$; and,
   d) HDH$^{leaky}$, HK$^{leaky}$ and AEC$^r$.

12. The process according to claim 7, wherein said sugar comprises at least one of sucrose, glucose, maltose and fructose.

* * * * *